(12) United States Patent
Wegner

(10) Patent No.: US 11,596,388 B2
(45) Date of Patent: *Mar. 7, 2023

(54) SPREAD SPECTRUM CODED WAVEFORMS IN ULTRASOUND DIAGNOSTICS

(71) Applicant: Decision Sciences International Corporation, Poway, CA (US)

(72) Inventor: Allan Wegner, Del Mar, CA (US)

(73) Assignee: Decision Sciences International Corporation, Poway, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/242,477

(22) Filed: Apr. 28, 2021

(65) Prior Publication Data
US 2021/0353259 A1 Nov. 18, 2021

Related U.S. Application Data

(63) Continuation of application No. 16/149,061, filed on Oct. 1, 2018, now Pat. No. 10,993,699, which is a
(Continued)

(51) Int. Cl.
*A61B 8/08* (2006.01)
*G01S 15/89* (2006.01)
(Continued)

(52) U.S. Cl.
CPC ............ *A61B 8/5207* (2013.01); *A61B 5/725* (2013.01); *A61B 8/145* (2013.01); *A61B 8/4483* (2013.01);
(Continued)

(58) Field of Classification Search
CPC ....... A61B 5/725; A61B 8/145; A61B 8/4483; A61B 8/4488; A61B 8/4494; A61B 8/463;
(Continued)

(56) References Cited

U.S. PATENT DOCUMENTS

| | | |
|---|---|---|
| 4,105,018 A | 8/1978 | Greenleaf et al. |
| 4,110,755 A | 8/1978 | Zottl |

(Continued)

FOREIGN PATENT DOCUMENTS

| | | |
|---|---|---|
| CA | 2427186 A1 | 5/2001 |
| CA | 2852801 A1 | 5/2013 |

(Continued)

OTHER PUBLICATIONS

Callow, H.J., "Signal Processing for Synthetic Aperture Sonar Image Enhancement," Thesis for Ph.D. in Electrical and Electronic Engineering at the University of Canterbury, Christchurch, New Zealand, 273 pages, Apr. 2003.

(Continued)

*Primary Examiner* — Michael T Rozanski
(74) *Attorney, Agent, or Firm* — Perkins Coie LLP

(57) ABSTRACT

Techniques, systems, and devices are disclosed for ultrasound diagnostics using spread spectrum, coherent, frequency- and/or phase-coded waveforms. In one aspect, a method includes synthesizing individual orthogonal coded waveforms to form a composite waveform for transmission toward a biological material of interest, in which the synthesized individual orthogonal coded waveforms correspond to distinct frequency bands and include one or both of frequency-coded or phase-coded waveforms; transmitting a composite acoustic waveform toward the biological material of interest, where the transmitting includes transducing the individual orthogonal coded waveforms into corresponding acoustic waveforms to form the composite acoustic waveform; receiving acoustic waveforms returned from at least part of the biological material of interest corresponding to at least some of the transmitted acoustic waveforms that form the composite acoustic waveform; and processing the
(Continued)

received returned acoustic waveforms to produce an image of at least part of the biological material of interest.

18 Claims, 6 Drawing Sheets

Related U.S. Application Data continuation of application No. 15/876,081, filed on Jan. 19, 2018, now Pat. No. 10,085,722, which is a continuation of application No. 15/236,229, filed on Aug. 12, 2016, now Pat. No. 9,872,667, which is a continuation of application No. 14/604,612, filed on Jan. 23, 2015, now Pat. No. 9,420,999, which is a continuation of application No. 13/663,100, filed on Oct. 29, 2012, now Pat. No. 8,939,909.

(60) Provisional application No. 61/553,137, filed on Oct. 28, 2011.

(51) Int. Cl.
  *A61B 8/00* (2006.01)
  *G01S 7/52* (2006.01)
  *A61B 8/14* (2006.01)
  *A61B 5/00* (2006.01)

(52) U.S. Cl.
  CPC .......... *A61B 8/4488* (2013.01); *A61B 8/4494* (2013.01); *A61B 8/463* (2013.01); *A61B 8/467* (2013.01); *A61B 8/488* (2013.01); *A61B 8/5223* (2013.01); *A61B 8/54* (2013.01); *G01S 7/5202* (2013.01); *G01S 7/52047* (2013.01); *G01S 15/8915* (2013.01); *G01S 15/8952* (2013.01); *G01S 15/8959* (2013.01); *G01S 7/52071* (2013.01); *G01S 15/8927* (2013.01); *G01S 15/8979* (2013.01)

(58) Field of Classification Search
  CPC ....... A61B 8/467; A61B 8/488; A61B 8/5207; A61B 8/5223; A61B 8/54; G01S 15/8915; G01S 15/8927; G01S 15/8952; G01S 15/8959; G01S 15/8979; G01S 7/5202; G01S 7/52047; G01S 7/52071
  See application file for complete search history.

(56) References Cited

U.S. PATENT DOCUMENTS

| | | |
|---|---|---|
| 4,159,462 A | 6/1979 | Rocha et al. |
| 4,277,367 A | 7/1981 | Madsen et al. |
| 4,437,468 A | 3/1984 | Sorenson |
| 4,463,608 A | 8/1984 | Takeuchi et al. |
| 4,620,546 A | 11/1986 | Aida et al. |
| 4,821,206 A | 4/1989 | Arora |
| 4,830,015 A | 5/1989 | Okazaki |
| 4,888,746 A | 12/1989 | Wurster et al. |
| 5,005,418 A | 4/1991 | Anderson |
| 5,039,774 A | 8/1991 | Shikinami et al. |
| 5,181,513 A | 1/1993 | Touboul et al. |
| 5,241,964 A | 9/1993 | McQuilkin |
| 5,269,309 A | 12/1993 | Fort et al. |
| 5,284,143 A | 2/1994 | Rattner |
| 5,329,944 A | 7/1994 | Fabian et al. |
| 5,394,877 A | 3/1995 | Orr et al. |
| 5,417,218 A | 5/1995 | Spivey et al. |
| 5,445,144 A | 8/1995 | Wodicka et al. |
| 5,465,722 A | 11/1995 | Fort et al. |
| 5,522,878 A | 6/1996 | Montecalvo |
| 5,533,510 A | 7/1996 | Koch, III et al. |
| 5,608,690 A | 3/1997 | Hossack et al. |
| 5,623,928 A | 4/1997 | Wright et al. |
| 5,682,886 A | 11/1997 | Delp et al. |
| 5,793,701 A | 8/1998 | Wright et al. |
| 5,800,356 A | 9/1998 | Criton et al. |
| 5,803,089 A | 9/1998 | Ferre et al. |
| 5,806,518 A | 9/1998 | Mittelstadt |
| 5,829,444 A | 11/1998 | Ferre et al. |
| 5,868,676 A | 2/1999 | McCabe et al. |
| 5,873,830 A | 2/1999 | Hossack et al. |
| 5,882,557 A | 3/1999 | Hayakawa et al. |
| 5,902,244 A | 5/1999 | Kobayashi et al. |
| 5,913,823 A | 6/1999 | Hedberg et al. |
| 5,967,980 A | 10/1999 | Ferre et al. |
| 6,016,285 A | 1/2000 | Wright et al. |
| 6,039,694 A | 3/2000 | Larson |
| 6,045,507 A | 4/2000 | Muzilla et al. |
| 6,050,945 A | 4/2000 | Peterson et al. |
| 6,083,164 A | 7/2000 | Oppelt et al. |
| 6,106,464 A | 8/2000 | Bass et al. |
| 6,110,114 A | 8/2000 | Nock et al. |
| 6,113,544 A | 9/2000 | Mo |
| 6,123,669 A | 9/2000 | Kanda |
| 6,132,375 A | 10/2000 | Napolitano |
| 6,157,592 A | 12/2000 | Kriz et al. |
| 6,205,411 B1 | 3/2001 | DiGioia, III et al. |
| 6,231,834 B1 | 5/2001 | Unger et al. |
| 6,241,676 B1 | 6/2001 | Savord |
| 6,322,567 B1 | 11/2001 | Mittelstadt et al. |
| 6,338,765 B1 | 1/2002 | Statnikov |
| 6,340,363 B1 | 1/2002 | Bolger et al. |
| 6,341,231 B1 | 1/2002 | Ferre et al. |
| 6,402,707 B1 | 6/2002 | Ernst |
| 6,425,865 B1 | 7/2002 | Salcudean et al. |
| 6,436,045 B1 | 8/2002 | Rafter et al. |
| 6,445,943 B1 | 9/2002 | Ferre et al. |
| 6,508,766 B2 | 1/2003 | Sato et al. |
| 6,537,216 B1 | 3/2003 | Shifrin |
| 6,583,392 B2 | 6/2003 | Hershey et al. |
| 6,585,648 B1 | 7/2003 | Robinson |
| 6,620,101 B2 | 9/2003 | Azzam et al. |
| 6,626,916 B1 | 9/2003 | Yeung et al. |
| 6,652,461 B1 | 11/2003 | Levkovitz |
| 6,687,531 B1 | 2/2004 | Ferre et al. |
| 6,725,082 B2 | 4/2004 | Sati et al. |
| 6,736,780 B2 | 5/2004 | Song et al. |
| 6,757,582 B2 | 6/2004 | Brisson et al. |
| 6,785,571 B2 | 8/2004 | Glossop |
| 6,786,097 B2 | 9/2004 | Song et al. |
| 6,796,988 B2 | 9/2004 | Melkent et al. |
| 6,808,494 B2 | 10/2004 | Shifrin |
| 6,843,957 B2 | 1/2005 | Statnikov |
| 6,918,877 B2 | 7/2005 | Hossack et al. |
| 6,934,575 B2 | 8/2005 | Ferre et al. |
| 6,939,300 B2 | 9/2005 | Petersen et al. |
| 6,960,173 B2 | 11/2005 | Babaev |
| 7,004,906 B1 | 2/2006 | Guracar et al. |
| 7,066,886 B2 | 6/2006 | Song et al. |
| 7,207,939 B2 | 4/2007 | Husher |
| 7,226,456 B2 | 6/2007 | O'Neil et al. |
| 7,291,119 B1 | 11/2007 | de Guise et al. |
| 7,344,609 B2 | 3/2008 | Statnikov |
| 7,395,181 B2 | 7/2008 | Foxlin |
| 7,473,250 B2 | 1/2009 | Makin et al. |
| 7,532,201 B2 | 5/2009 | Quistgaard et al. |
| 7,542,790 B2 | 6/2009 | Jensen et al. |
| 7,566,304 B2 | 7/2009 | Nakamura et al. |
| 7,601,966 B2 | 10/2009 | Ben-Haim |
| 7,678,049 B2 | 3/2010 | Tsoref et al. |
| 7,719,515 B2 | 5/2010 | Fujiwara et al. |
| 7,719,689 B2 | 5/2010 | Lee et al. |
| 7,728,487 B2 | 6/2010 | Adachi et al. |
| 7,763,035 B2 | 7/2010 | Melkent et al. |
| 7,798,585 B2 | 9/2010 | Oguri |
| 7,806,823 B2 | 10/2010 | Sakai et al. |
| 7,826,889 B2 | 11/2010 | David et al. |
| 7,835,778 B2 | 11/2010 | Foley et al. |
| 7,835,784 B2 | 11/2010 | Mire et al. |
| 7,837,625 B2 | 11/2010 | Abe |
| RE42,194 E | 3/2011 | Foley et al. |
| 7,905,836 B2 | 3/2011 | Dan |

(56) References Cited

U.S. PATENT DOCUMENTS

| | | |
|---|---|---|
| 7,917,317 B2 | 3/2011 | McKeon |
| 7,938,777 B2 | 5/2011 | Amiot et al. |
| 7,938,778 B2 | 5/2011 | Sakai |
| 7,982,362 B2 | 7/2011 | Adachi et al. |
| 8,002,705 B1 | 8/2011 | Napolitano et al. |
| 8,038,616 B2 | 10/2011 | Angelsen et al. |
| 8,043,220 B2 | 10/2011 | Okada et al. |
| 8,103,461 B2 | 1/2012 | Glaser et al. |
| 8,105,339 B2 | 1/2012 | Melkent et al. |
| 8,126,533 B2 | 2/2012 | Lavallee |
| 8,147,409 B2 | 4/2012 | Shifrin |
| 8,152,726 B2 | 4/2012 | Amiot et al. |
| 8,165,658 B2 | 4/2012 | Waynik et al. |
| 8,241,217 B2 | 8/2012 | Chiang et al. |
| 8,251,908 B2 | 8/2012 | Vortman et al. |
| 8,253,578 B2 | 8/2012 | Watabe et al. |
| 8,311,611 B2 | 11/2012 | Csavoy et al. |
| 8,323,200 B2 | 12/2012 | Kunita |
| 8,372,070 B2 | 2/2013 | Tanaka et al. |
| 8,374,674 B2 | 2/2013 | Gertner |
| 8,409,099 B2 | 4/2013 | Vitek et al. |
| 8,409,103 B2 | 4/2013 | Grunwald et al. |
| 8,444,564 B2 | 5/2013 | Mahfouz et al. |
| 8,447,388 B2 | 5/2013 | Igarashi |
| 8,491,476 B2 | 7/2013 | Iwama et al. |
| 8,556,834 B2 | 10/2013 | Gertner |
| 8,565,860 B2 | 10/2013 | Kimchy et al. |
| 8,626,267 B2 | 1/2014 | Lavallee |
| 8,675,939 B2 | 3/2014 | Moctezuma de la Barrera |
| 8,771,188 B2 | 7/2014 | Schers et al. |
| 8,774,900 B2 | 7/2014 | Buly et al. |
| 8,814,810 B2 | 8/2014 | Roche et al. |
| 8,864,686 B2 | 10/2014 | Roche et al. |
| 8,880,152 B2 | 11/2014 | Lavallee |
| 8,909,325 B2 | 12/2014 | Kimchy et al. |
| 8,939,909 B2 | 1/2015 | Wegner |
| 9,060,794 B2 | 6/2015 | Kang et al. |
| 9,101,394 B2 | 8/2015 | Arata et al. |
| 9,127,998 B1 | 9/2015 | Guldiken |
| 9,174,065 B2 | 11/2015 | Gertner |
| 9,196,046 B2 | 11/2015 | Meyer |
| 9,220,571 B2 | 12/2015 | Lavallee |
| 9,244,169 B2 | 1/2016 | Fan et al. |
| 9,248,001 B2 | 2/2016 | Colombet et al. |
| 9,352,171 B2 | 5/2016 | Gertner |
| 9,387,276 B2 | 7/2016 | Sun et al. |
| 9,420,999 B2 | 8/2016 | Wegner |
| 9,572,548 B2 | 2/2017 | Moctezuma de la Barrera |
| 9,597,058 B2 | 3/2017 | Kanayama et al. |
| 9,844,359 B2 | 12/2017 | Wegner |
| 9,872,667 B2 | 1/2018 | Wegner |
| 10,085,722 B2 | 10/2018 | Wegner |
| 10,321,889 B2 | 6/2019 | Wegner |
| 10,426,429 B2 | 10/2019 | Kruse et al. |
| 10,993,699 B2 | 5/2021 | Wegner |
| 2002/0068871 A1 | 6/2002 | Mendlein et al. |
| 2002/0099290 A1 | 7/2002 | Haddad |
| 2002/0122536 A1 | 9/2002 | Kerrien et al. |
| 2002/0188198 A1 | 12/2002 | Hong |
| 2002/0188229 A1 | 12/2002 | Ryaby et al. |
| 2003/0036702 A1 | 2/2003 | Davidsen |
| 2003/0125628 A1 | 7/2003 | Song et al. |
| 2003/0233045 A1 | 12/2003 | Vaezy |
| 2004/0066708 A1 | 4/2004 | Ogawa |
| 2004/0236223 A1 | 11/2004 | Barnes et al. |
| 2005/0101861 A1 | 5/2005 | Satoh |
| 2005/0101867 A1 | 5/2005 | Johnson et al. |
| 2005/0154302 A1 | 7/2005 | Sela et al. |
| 2005/0203399 A1 | 9/2005 | Vaezy |
| 2005/0215893 A1 | 9/2005 | Barnes et al. |
| 2006/0004290 A1 | 1/2006 | Smith et al. |
| 2006/0119223 A1 | 6/2006 | Ossmann |
| 2006/0173305 A1 | 8/2006 | Asafusa et al. |
| 2007/0066897 A1 | 3/2007 | Sekins et al. |
| 2007/0156050 A1 | 7/2007 | Barnes et al. |
| 2007/0226976 A1 | 10/2007 | Zipparo et al. |
| 2007/0239001 A1 | 10/2007 | Mehi et al. |
| 2007/0239002 A1 | 10/2007 | Alam |
| 2007/0265690 A1 | 11/2007 | Lichtenstein et al. |
| 2007/0276238 A1 | 11/2007 | Sudol |
| 2008/0110263 A1 | 5/2008 | Klessel et al. |
| 2008/0119737 A1 | 5/2008 | Urbano et al. |
| 2008/0200810 A1 | 8/2008 | Buchalter |
| 2008/0208055 A1 | 8/2008 | Bertram et al. |
| 2008/0262347 A1 | 10/2008 | Batchelder et al. |
| 2008/0281202 A1 | 11/2008 | Fraser et al. |
| 2008/0281237 A1 | 11/2008 | Slayton et al. |
| 2009/0043206 A1 | 2/2009 | Towfiq et al. |
| 2009/0093737 A1 | 4/2009 | Chomas |
| 2009/0124871 A1 | 5/2009 | Arshak et al. |
| 2009/0306497 A1 | 12/2009 | Manzke et al. |
| 2010/0179425 A1 | 7/2010 | Zadicario |
| 2010/0204577 A1 | 8/2010 | Sekins et al. |
| 2010/0268072 A1 | 10/2010 | Hall et al. |
| 2010/0274139 A1 | 10/2010 | Fukukita et al. |
| 2010/0280379 A1 | 11/2010 | Satoh |
| 2010/0286518 A1 | 11/2010 | Lee et al. |
| 2010/0286527 A1 | 11/2010 | Cannon |
| 2011/0060226 A1 | 3/2011 | Yen et al. |
| 2011/0092862 A1 | 4/2011 | Chivers |
| 2011/0264012 A1 | 10/2011 | Lautzenhiser et al. |
| 2012/0029345 A1 | 2/2012 | Mahfouz et al. |
| 2012/0238875 A1 | 9/2012 | Savitsky et al. |
| 2012/0281507 A1 | 11/2012 | Rikoski |
| 2013/0060121 A1 | 3/2013 | Patwardhan et al. |
| 2013/0144135 A1 | 6/2013 | Mahfouz et al. |
| 2013/0144166 A1 | 6/2013 | Specht et al. |
| 2013/0150863 A1 | 6/2013 | Baumgartner |
| 2013/0165005 A1 | 6/2013 | Berard-Andersen et al. |
| 2013/0218013 A1 | 8/2013 | Barthe et al. |
| 2014/0163377 A1 | 6/2014 | Kang et al. |
| 2014/0180116 A1 | 6/2014 | Lindekugel et al. |
| 2015/0018682 A1 | 1/2015 | Schers et al. |
| 2015/0038613 A1 | 2/2015 | Sun et al. |
| 2015/0088040 A1 | 3/2015 | Barthe et al. |
| 2015/0133788 A1 | 5/2015 | Mauldin, Jr. et al. |
| 2015/0164467 A1 | 6/2015 | Suetoshi et al. |
| 2015/0182191 A1 | 7/2015 | Caluser et al. |
| 2015/0313572 A1 | 11/2015 | Gerbaulet et al. |
| 2015/0359512 A1 | 12/2015 | Boctor et al. |
| 2016/0000409 A1 | 1/2016 | Bruder et al. |
| 2016/0100821 A1 | 4/2016 | Eggers et al. |
| 2016/0176128 A1 | 6/2016 | Zhao et al. |
| 2016/0242736 A1 | 8/2016 | Freiburg et al. |
| 2016/0270763 A1 | 9/2016 | Hayes et al. |
| 2018/0126677 A1 | 5/2018 | Zhao et al. |
| 2019/0200957 A1 | 7/2019 | Freiburg et al. |
| 2020/0029931 A1 | 1/2020 | Kruse et al. |
| 2020/0029933 A1 | 1/2020 | Wegner |
| 2020/0284902 A1 | 9/2020 | Kruse et al. |
| 2020/0337674 A1 | 10/2020 | Wegner |
| 2022/0087642 A1 | 3/2022 | Wegner |
| 2022/0192634 A1 | 6/2022 | Freiburg et al. |

FOREIGN PATENT DOCUMENTS

| | | |
|---|---|---|
| CN | 100354651 C | 12/2007 |
| CN | 101325913 | 12/2008 |
| CN | 102258399 B | 11/2012 |
| CN | 104169739 A | 11/2014 |
| EP | 0952461 A2 | 10/1999 |
| EP | 1707124 A2 | 4/2006 |
| EP | 1795917 A2 | 6/2007 |
| EP | 1854406 A1 | 11/2007 |
| EP | 1955668 A1 | 8/2008 |
| EP | 2033579 A1 | 3/2009 |
| GB | 2379392 | 3/2003 |
| GB | 2472066 A | 1/2011 |
| IL | 232148 A | 7/2019 |
| JP | 55051351 A | 4/1980 |
| JP | 58195550 A | 11/1983 |
| JP | 60048736 A | 3/1985 |
| JP | 62117535 A | 5/1987 |
| JP | 08038473 A | 2/1996 |

(56) References Cited

FOREIGN PATENT DOCUMENTS

| | | | |
|---|---|---|---|
| JP | 2000041980 A | 2/2000 | |
| JP | 2000166922 A | 6/2000 | |
| JP | 2000287988 A | 10/2000 | |
| JP | 2003190157 A | 7/2003 | |
| JP | 2004147852 A | 5/2004 | |
| JP | 2005152608 A | 6/2005 | |
| JP | 2005527336 | 9/2005 | |
| JP | 2007152127 A | 6/2007 | |
| JP | 2010082425 A | 4/2010 | |
| JP | 2011062531 A | 3/2011 | |
| JP | 2011177461 A | 9/2011 | |
| JP | 2012002586 A | 1/2012 | |
| JP | 2013056156 A | 3/2013 | |
| JP | 2013520235 | 6/2013 | |
| JP | 2013539715 A | 10/2013 | |
| JP | 2014533154 A | 12/2014 | |
| WO | 2002024094 A2 | 3/2002 | |
| WO | 2007023477 A2 | 3/2007 | |
| WO | 2007069156 | 6/2007 | |
| WO | 2009009064 A1 | 1/2009 | |
| WO | 2009020617 A1 | 2/2009 | |
| WO | 2009063421 A1 | 5/2009 | |
| WO | 2013066821 A2 | 5/2013 | |
| WO | 2013103956 A1 | 7/2013 | |
| WO | 2014128593 A1 | 8/2014 | |
| WO | 2014150780 A2 | 9/2014 | |
| WO | 2014150961 A1 | 9/2014 | |
| WO | 2014186904 A1 | 11/2014 | |
| WO | 2015038554 A2 | 3/2015 | |
| WO | 2016044830 A1 | 3/2016 | |
| WO | 2016138257 A1 | 9/2016 | |
| WO | 2016149427 A1 | 9/2016 | |
| WO | 2014103512 | 1/2017 | |

OTHER PUBLICATIONS

Cao, Z. et al., "Fabrication and properties of thermosensitive organic/inorganic hybrid hydrogel thin films," Langmuir, American Chemical Society, vol. 24, No. 10, May 20, 2008, pp. 5543-5551.
Chiao, R., "Coded Excitation for Diagnostic Ultrasound: A System Developer's Perspective," *IEEE Transactions on Ultrasonics, Ferroelectrics, and Frequency Control*, 52(2):160-170, Feb. 2005.
Choe, J.W., et al., "Volumetric real-time imaging using a CMUT ring array," IEEE Transactions on Ultrasonics, Ferroelectrics, and Frequency Control, 59(6):1201-1211, Jun. 2012.
Demi, L., et al., "In Vitro and In Vivo Tissue Harmonic Images Obtained With Parallel Transmit Beamforming by Means of Orthogonal Frequency Division Multiplexing," IEEE Transactions on Ultrasonics, Ferroelectrics, and Frequency Control, 62(1):230-235, Jan. 2015.
European Search Report dated Apr. 19, 2017 for European Application No. 14844538.0, filed on Sep. 9, 2014 (10 pages).
European Search Report dated Feb. 1, 2019 for European Application No. 16756353.5, filed on Feb. 25, 2016 (14 pages).
European Search Report dated Jun. 29, 2015 for European Application No. 12845256.2, filed on Oct. 29, 2012 (8 pages).
European Search Report dated Nov. 9, 2018 for European Application No. 16765701.4, filed on Mar. 16, 2016 (6 pages).
Exam Report dated Nov. 1, 2019 for Australian Application No. 2016233279, filed on Mar. 16, 2016 (3 pages).
Exam Report dated Oct. 18, 2019 for Australian Application No. 2016222637, filed on Feb. 25, 2016 (3 pages).
Exam Report dated Feb. 26, 2019 for Singapore Application No. 11201706953Y, filed on Feb. 25, 2016 (6 pages).
Examination Report dated Dec. 20, 2019 for Europe Patent Application No. 14844538.0, filed on Sep. 9, 2014 (7 pages).
Examination Report dated Jul. 26, 2018 for Canada Patent Application No. 2,852,801, filed on Oct. 29, 2012, 4 pages.
Examination Report dated Jun. 22, 2020 for Australian Application No. 2016334258, 4 pages.
Examination Report dated Mar. 16, 2018 for European Application No. 12845256.2, filed on Oct. 29, 2012 (8 pages).
Examination Report dated Jul. 19, 2021 for European Application No. 12845256.2, filed on Oct. 29, 2012 (8 pages).
Extended European Search Report dated Feb. 15, 2019 for European Application No. 16765701.4, filed on Mar. 16, 2016 (14 pages).
Extended European Search Report dated Jul. 2, 2019 for European Application No. 16756353.5, filed on Feb. 25, 2016 (14 pages).
Extended European Search Report dated Jun. 18, 2019 for European Application No. 16854507.7, filed on Oct. 7, 2016 (11 pages).
First Examination Report dated Apr. 12, 2016 for Australian Patent Application No. 2012332817, filed on Oct. 29, 2012, 3 pages.
First Examination Report dated Nov. 21, 2018 for Australian Patent Application No. 2018203785, filed on Oct. 29, 2012, 2 pages.
First Office Action dated Aug. 14, 2020 for Chinese Patent Application No. 201680071645.1, with English translation, 35 pages.
Hunter, A.J., et al., "A Comparison of Fast Factorised Back-Projection and Wavenumber Algorithms for SAS Image Reconstruction," Proceedings of the World Congress on Ultrasonics, 4 pages, (2003).
International Search Report and Written Opinion dated Dec. 29, 2016 for International Application No. PCT/US2016/056159, filed on Oct. 7, 2016 (7 pages).
International Search Report and Written Opinion dated Jul. 6, 2016 for International Application No. PCT/US2016/019554, filed on Feb. 25, 2016 (12 pages).
International Search Report and Written Opinion dated Mar. 3, 2015 for International Application No. PCT/US2014/054855, filed on Sep. 9, 2014 (11 pages).
International Search Report and Written Opinion dated May 15, 2013 for International Application No. PCT/US2012/062435, filed on Oct. 29, 2012 (9 pages).
Ito, T., et al., "Evaluation of Acoustic Imaging System Using Correlation Division in Synthetic Transmit Aperture with Multicarrier Signals," IEICE Transactions on Fundamentals of Electronics, Communications and Computer Sciences, E94-A(10):1907-1919, Oct. 2011.
Jensen, J.A., et al., "Synthetic Aperture Ultrasound Imaging," Ultrasonics, 44(Suppl 1):e5-e15, Dec. 2006.
Koch, A., et al., "An Ultrasound Tomography System With Polyvinyl Alcohol (PVA) Moldings for Coupling: In Vivo Results for 3-D Pulse-Echo Imaging of the Female Breast," IEEE Transactions on Ultrasonics, Ferroelectrics, and Frequency Control, 62(2):266-279, Feb. 2015.
Kundur, D., et al., "A Novel Blind Deconvolution Scheme for Image Restoration Using Recursive Filtering," IEEE Transactions on Signal Processing, 46(2):375-390, Feb. 1998.
Misaridis, T., "Use of Modulated Excitation Signals in Medical Ultrasound. Part I: Basic Concepts and Expected Benefits," *IEEE Transactions on Ultrasonics, Ferroelectrics, and Frequency Control*, 52(2):177-191, Feb. 2005.
Misaridis, T., "Use of Modulated Excitation Signals in Medical Ultrasound. Part II: Design and Performance for Medical Imaging Applications," *IEEE Transactions on Ultrasonics, Ferroelectrics, and Frequency Control*, 52(2):192-207, Feb. 2005.
Misaridis, T., "Use of Modulated Excitation Signals in Medical Ultrasound. Part III: High Frame Rate Imaging," *IEEE Transactions on Ultrasonics, Ferroelectrics, and Frequency Control*, 52(2):208-219, Feb. 2005.
Notification of Defects dated Nov. 22, 2017 for Israel Patent Application No. 232148, filed on Oct. 29, 2012, 4 pages.
O'Donnell, M., "Coded Excitation for Synthetic Aperture Ultrasound Imaging," *IEEE Transactions on Ultrasonics, Ferroelectrics, and Frequency Control*, 52(2):171-176, Feb. 2005.
Office Action dated Aug. 30, 2020 for Israel Application No. 264906, filed on Oct. 29, 2012, with English translation, 10 pages.
Office Action dated Jan. 13, 2020 for Chinese Application No. 201680028663.1, filed on Mar. 16, 2016 (17 pages).
Office Action dated Jan. 14, 2020 for Japanese Application No. 2017-563504, filed on Feb. 25, 2016 (14 pages).
Office Action dated Jun. 3, 2021 for Israel Application No. 258533, 7 pages, with English Translation.

(56) References Cited

OTHER PUBLICATIONS

Office Action dated Jun. 4, 2019 for Japanese Application No. 2017-187288, filed on Oct. 29, 2012 (3 pages).
Office Action dated Mar. 17, 2020 for Japanese Application No. 2018-145683, filed on Sep. 9, 2014 (4 pages).
Office Action dated Mar. 25, 2020 for Japanese Application No. 2016-542050, filed on Sep. 9, 2014 (4 pages).
Office Action dated Oct. 20, 2020 for Canadian Application No. 2,923,861, 4 pages.
Office Action dated Oct. 29, 2019 for Japanese Application No. 2018-145683, filed on Sep. 9, 2014 (3 pages).
Office Action dated Dec. 4, 2019 for Chinese Application No. 201680023999.9, filed on Feb. 25, 2016 (23 pages).
Office Action dated Feb. 25, 2020 for Japanese Application No. 2017-549178, filed on Mar. 16, 2016 (8 pages).
Office Action dated Jul. 3, 2018 for Japanese Application No. 2017-187288, filed on Oct. 29, 2012 (6 pages).
Office Action dated Jun. 11, 2019 for Japanese Application No. 2016-542050, filed on Sep. 9, 2014 (15 pages).
Office Action dated Jun. 18, 2019 for Japanese Patent Application No. 2018-145683, filed on Sep. 9, 2014, 12 pages.
Office Action dated Jun. 5, 2018 for Chinese Patent Application No. 201480062224.3, filed on Sep. 9, 2014, 13 pages.
Office Action dated Sep. 13, 2016 for Japanese Application No. 2014-539114, filed on Oct. 29, 2012 (4 pages).
Office Action dated Sep. 19, 2017 for Japanese Application No. 2016-542050, filed on Sep. 9, 2014 (15 pages).
Office Action dated Sep. 2, 2015 for Chinese Application No. 201280065031.4, filed on Oct. 29, 2012 (26 pages).
Office Action dated Sep. 23, 2020 for Israel Application No. 254158, filed Feb. 25, 2016, english translation, 3 pages.
Prokop A F et al., "Polyacrylamide gel as an acoustic coupling medium for focused ultrasound therapy." Ultrasound in Medicine and Biol, New York, NY, US, vol. 29, No. 9, Sep. 1, 2003, pp. 1351-1358.
Rui Silva, S., et al., "2 Synthetic Aperture Techniques for Sonar Systems," Advances in Sonar Technology, edited by Sergio Rui Silva, publisher I-Tech Education and Publishing, ISBN 978-3-902613-48-6, pp. 15-42, Feb. 2009.
Second Office Action dated Jul. 14, 2020 for Chinese Patent Application No. 201680023999.9, filed on Feb. 25, 2016, 41 pages, with English translation.
Second Office Action dated Jul. 20, 2016 for Chinese Patent Application No. 201280065031.4, filed on Oct. 29, 2012 (26 pages).
Second Office Action dated Jun. 1, 2021 for Chinese Patent Application No. 201680071645.1, with English translation, 32 pages.
Singapore Search Report dated Sep. 24, 2018 for Singapore Application No. 11201706953Y, filed on Feb. 25, 2016 (13 pages).
Singapore Written Opinion dated Jul. 10, 2017 for Singapore Application No. 11201601906P, filed on Sep. 9, 2014 (8 pages).
Singapore Written Opinion dated Jun. 21, 2018 for Singapore Application No. 11201707641P, filed on Mar. 16, 2016 (8 pages).
Singapore Written Opinion dated Mar. 11, 2020 for Singapore Application No. 11201707641P, filed on Mar. 16, 2016 (8 pages).
Zhu, S., et al., "SAS Autofocus Based on Phase Gradient Autofocus," IEEE 2011 Fourth International Workshop on Chaos-Fractals Theories and Applications (IWCFTA), pp. 298-301, Oct. 19-22, 2011.
Australian Exam Report dated Oct. 18, 2019 for Australian Application No. 2016222637, filed on Feb. 25, 2016 (3 pages).
International Search Report and Written Opinion dated Feb. 4, 2022 in International Patent Application No. PCT/US21/59424, 19 pages.
Murphy, R.J. et al.,"Pose Estimation of Known Objects During Transmission Tomographic Image Reconstruction." IEEE Transactions on Medical Imaging, vol. 25, No. 10, Oct. 2006, 13 pages.
Office Action dated Oct. 7, 2021 in Israel Patent Application No. 254158, 6 pages, with English translation.
Principles of Computer Tomography. Textbook, Introduction, Chapter 1, and Chapter 8. Retrieved 1999, 39 pages.
Stayman, J.W. et al., "Model-Based Tomographic Reconstruction of Objects Containing Known Components." IEEE Transactions on Medical Imaging, vol. 31, No. 10, Oct. 2012, 12 pages.
Trots, I. et al., "Synthetic Aperture Method in Ultrasound Imaging," Chapter 3 of Ultrasound Imaging, edited by Masayuki Tanabe, 2011, pp. 37-56.
Wikipedia. Rotation matrix. Retrieved from the internet on Sep. 17, 2020 from <https//en.wikipedia.org/wiki?Rotation__matrix>, 26 pages.
Examination Report dated Oct. 4, 2022 in European Patent Application No. 14844538.0, 4 pages.
Examination Report dated Aug. 9, 2022 for European Patent Application No. 16854507.7, 8 pages.
Notice of Preliminary Rejection dated Jul. 28, 2022 for Korean Patent Application No. 10-2017-7027091, 22 pages.
Office Action dated Oct. 29, 2021 in Chinese Patent Application No. 201680071645.1, with English translation, 28 pages.

SPREAD SPECTRUM CODED WAVEFORMS IN ULTRASOUND DIAGNOSTICS

CROSS REFERENCE TO RELATED APPLICATIONS

This patent document is a continuation of U.S. patent application Ser. No. 16/149,061, filed on Oct. 1, 2018, which is a continuation of U.S. patent application Ser. No. 15/876,081, filed on Jan. 19, 2018, now U.S. Pat. No. 10,085,722, which is a continuation of U.S. patent application Ser. No. 15/236,229, filed on Aug. 12, 2016, now U.S. Pat. No. 9,872,667, which is a continuation of U.S. patent application Ser. No. 14/604,612, filed on Jan. 23, 2015, now U.S. Pat. No. 9,420,999, which is a continuation of U.S. patent application Ser. No. 13/663,100, filed on Oct. 29, 2012, now U.S. Pat. No. 8,939,909, which claims the benefit of priority of U.S. Provisional Patent Application No. 61/553,137, filed on Oct. 28, 2011. The entire contents of the before-mentioned patent applications are incorporated by reference as part of the disclosure of this document.

TECHNICAL FIELD

This patent document relates to systems and processes for ultrasound diagnostics.

BACKGROUND

Ultrasound imaging is an imaging modality that employs the properties of sound waves traveling through a medium to render a visual image. Ultrasound imaging has been used as an imaging modality for decades in a variety of biomedical fields to view internal structures and functions of animals and humans. Ultrasound waves used in biomedical imaging may operate in different frequencies, e.g., between 1 and 20 MHz, or even higher frequencies. Some factors including inadequate spatial resolution and tissue differentiation can lead to less than desirable image quality using conventional techniques of ultrasound imaging, which can limit its use for many clinical applications.

SUMMARY

Techniques, systems, and apparatuses are disclosed for ultrasound diagnostics using spread spectrum, coherent, frequency- and/or phase-coded waveforms that can exhibit wide instantaneous bandwidth.

In one aspect of the disclosed technology, a method of creating an image from an acoustic waveform in an acoustic imaging device includes setting a transmit/receive switch in the acoustic imaging device into a transmit mode to transmit an acoustic waveform toward a target, in transmitting the acoustic waveform, synthesizing, in one or more waveform synthesizers, a plurality of substantially orthogonal coded waveforms that form a composite waveform as the transmitted acoustic waveform toward the target, in which each waveform corresponds to a distinct frequency band and the coded waveforms include at least one of frequency-coded waveforms or phase-coded waveforms, setting the transmit/receive switch in the acoustic imaging device into a receive mode to receive a returned acoustic waveform that returns from at least part of the target, converting the received returned acoustic waveform from analog format to digital format as a received composite waveform comprising information of the target, and processing the received composite waveform to produce an image of at least part of the target.

In another aspect, an acoustic waveform imaging system is provided to include waveform generation unit comprising one or more waveform synthesizers coupled to a waveform generator, wherein the waveform generation unit synthesizes a composite waveform comprising a plurality of substantially orthogonal coded waveforms corresponding to frequency bands that are generated by the one or more waveform synthesizers according to waveform information provided by the waveform generator, the coded waveforms including at least one of frequency-coded waveforms or phase-coded waveforms; a transmit/receive switching unit that switches between a transmit mode and a receive mode; an array of transducer elements in communication with the transmit/receive switching unit that transmits an acoustic waveform based on the composite waveform toward a target and receives a returned acoustic waveform returned from at least part of the target; an array of analog to digital (A/D) converters to convert the received returned acoustic waveform received by the array of transducer elements from analog format to digital format as a received composite waveform comprising information comprising information of the target; a controller unit in communication with the waveform generation unit and the array of A/D converters comprising a processing unit that processes the received composite waveform to produce an image of at least part of the target; and a user interface unit in communication with the controller unit.

In another aspect, a method of creating an image from an acoustic waveform is provided to include setting a transmit/receive switch into transmit mode; selecting a mode of operation from a plurality of operating modes; synthesizing, in one or more waveform synthesizers, a plurality of substantially orthogonal coded waveforms that form a composite waveform, wherein each waveform corresponds to a distinct frequency band, the coded waveforms including at least one of frequency-coded waveforms or phase-coded waveforms; transmitting an acoustic waveform based on the composite waveform toward a target; setting the transmit/receive switch into receive mode; receiving a returned acoustic waveform returned from at least part of the target; converting the received returned acoustic waveform from analog format to digital format as a received composite waveform comprising information of the target; and processing the received composite waveform to produce an image of at least part of the target.

In another aspect, a method of creating an image from an acoustic waveform is provided to include combining a plurality of coded waveforms corresponding to different frequency bands to produce a composite waveform comprising substantially orthogonal wave signals at the different frequency bands, the coded waveforms including at least one of frequency-coded waveforms or phase-coded waveforms; using the composite waveform to produce an acoustic probe wave that includes the different frequency bands toward a target; receiving acoustic energy returned from at least part of the target after the acoustic probe wave is sent to the target; converting the received returned acoustic energy into a digital composite waveform comprising information of the target; and processing the received composite waveform to produce an image of at least part of the target.

In yet another aspect, a device for creating an image from an acoustic waveform is provided to include means for combining a plurality of coded waveforms corresponding to different frequency bands to produce a composite waveform comprising substantially orthogonal wave signals at the different frequency bands, the coded waveforms including at least one of frequency-coded waveforms or phase-coded waveforms; means for using the composite waveform to produce an acoustic probe wave that includes the different frequency bands toward a target; means for receiving acoustic energy returned from at least part of the target after the acoustic probe wave is sent to the target; means for converting the received returned acoustic energy into a digital composite waveform comprising information of the target; and means for processing the received composite waveform to produce an image of at least part of the target.

The subject matter described in this patent document can provide one or more of the following features and be used in many applications. For example, the disclosed technology can be used during routine primary care screenings to identify and locate early stage malignancies, as well as later stage cancers, which can potentially raise survival rates of hard to diagnose asymptomatic patients. The disclosed technology can be used by board certified radiologists to diagnose neoplasms as benign or malignant prior to any surgical biopsy or resection intervention, which may also improve patient survival rate while reducing unnecessary biopsies. The disclosed technology can, when integrated with a fine needle biopsy instrument, be used in medical procedures to confirm noninvasive diagnoses, which can reduce the level of invasiveness of such biopsy procedures. The disclosed technology can, when integrated with minimally invasive surgical high definition video instrumentation, fuse optical and ultrasound images, which can further give surgeons added abilities to locate and surgically excise diseased tissue without excising excessive healthy tissue. The disclosed technology can, when integrated with specialized surgical instrumentation, fusing ultrasound images with other data, can give surgeons added abilities to locate and manipulate anatomic areas of interest while minimizing unnecessary damage to nearby structures. The disclosed technology can reduce the amount of time for the brachytherapy treatment of malignant neoplasms by, for example, precisely guiding the insertion of catheters and sealed radioactive sources into the proper location. Similarly, the disclosed technology can aid insertion of high dose, localized pharmaceuticals for treatments of diseases.

BRIEF DESCRIPTION OF THE DRAWINGS

Like reference symbols and designations in the various drawings indicate like elements.

DETAILED DESCRIPTION

Techniques, systems, and apparatuses are described for generating, transmitting, receiving, and processing coherent spread spectrum frequency- and/or phase-coded waveforms used in ultrasound diagnostics.

Ultrasound imaging can be performed by emitting a time-gated, single frequency or narrow instantaneous bandwidth acoustic waveform (pulse), which is partly reflected from a boundary between two mediums (e.g., biological tissue structures) and partially transmitted. The reflection can depend on the acoustic impedance difference between the two mediums. Ultrasound imaging by some techniques may only use amplitude information from the reflected signal. For example, when one pulse is emitted, the reflected signal can be sampled continuously. In biological tissue, sound velocity can be considered fairly constant, in which the time between the emission of a waveform and the reception of a reflected signal is dependent on the distance the waveform travels in that tissue structure (e.g., the depth of the reflecting structure). Therefore, reflected signals may be sampled at multiple time intervals to receive the reflected signals being reflected from multiple depths. Also, different tissues at the different depths can partially reflect the incident waveform with different amounts of energy, and thus the reflected signal from different mediums can have different amplitudes. A corresponding ultrasound image can be constructed based on depth. The time before a new waveform is emitted can therefore be dependent of the maximum depth that is desired to image. Ultrasound imaging techniques employing pulsed monochromatic and/or narrow instantaneous bandwidth waveforms can suffer from poor resolution of image processing and production. Yet, waveforms with spread spectrum, wide instantaneous bandwidth characteristics that can be coded (e.g., by frequency and/or phase) can enable real-time control of ultrasound imaging and higher quality resultant images.

Figure 1A:
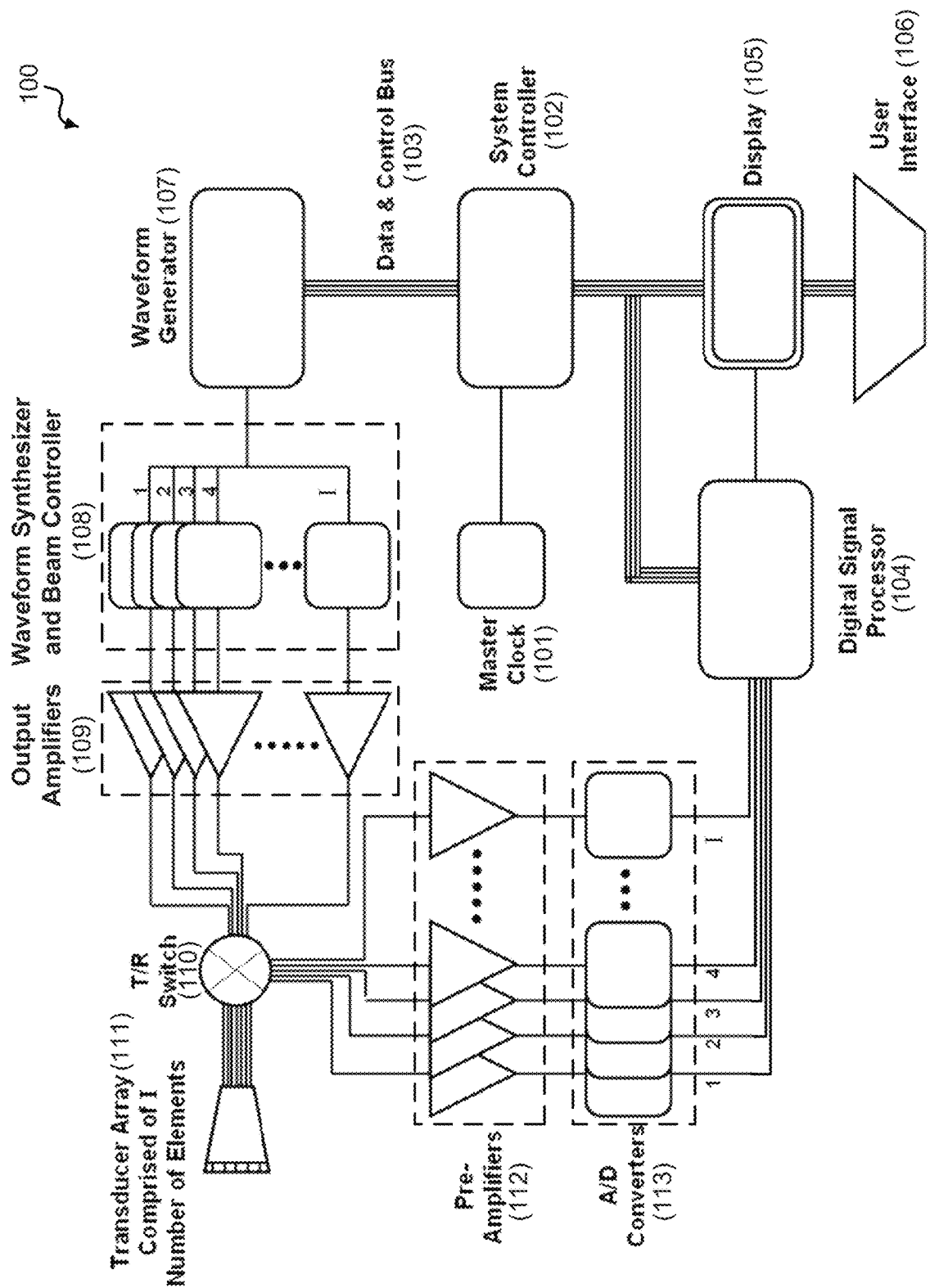
FIG. 1A shows a block diagram of an exemplary ultrasound imaging system using spread spectrum coded waveforms.

FIG. 1A shows a block diagram of an exemplary ultrasound system (100) that can produce acoustic waveforms with enhanced waveform properties that include a spread-spectrum, wide instantaneous bandwidth, coherency, pseudo-random noise characteristics, and frequency- and/or phase-coding. System (100) can be configured in one of many system designs. In one example, system (100) can include a Master Clock (101) for time synchronization. The Master Clock (101) can be interfaced with a System Controller (102). System Controller (102) can include a processing unit, e.g., a central processing unit (CPU) of RISC-based or other types of CPU architectures. System Controller (102) can also include at least one input/output (I/O) unit(s) and/or memory unit(s), which are in communication with the processing unit, to support various functions of the System Controller (102). For example, the processing unit can be associated with a system control bus, e.g., Data & Control Bus (103). System Controller (102) can be implemented as one of various data processing architectures, such as a personal computer (PC), laptop, tablet, and mobile communication device architectures.

The memory unit(s) can store other information and data, such as instructions, software, values, images, and other data processed or referenced by the processing unit. Various types of Random Access Memory (RAM) devices, Read Only Memory (ROM) devices, Flash Memory devices, and other suitable storage media can be used to implement storage functions of the memory unit(s). The memory unit(s) can store pre-stored waveforms and coefficient data and information, which can be used in the implementation of generating a waveform, e.g., such as a spread-spectrum, wide instantaneous bandwidth, coherent, pseudo-random noise, and frequency and/or phase-coded waveform. The memory unit(s) can store data and information obtained from received and processed waveforms, which can be used to generate and transmit new waveforms. The memory unit(s) can be associated with a system control bus, e.g., Data & Control Bus (103).

The I/O unit(s) can be connected to an external interface, source of data storage, and/or display device. The I/O unit(s) can be associated with a system control bus, e.g., Data & Control Bus (103). Various types of wired or wireless interfaces compatible with typical data communication standards, such as but not limited to Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), and parallel interfaces, can be used to implement the I/O unit. The I/O unit can interface with an external interface, source of data storage, or display device to retrieve and transfer data and information that can be processed by the processor unit, stored in the memory unit, or exhibited on an output unit.

System Controller (102) can control all of the modules of system (100), e.g., through connection via Data & Control Bus (103). For example, Data & Control Bus (103) can link System Controller (102) to one or more attached digital signal processors, e.g., Digital Signal Processor (104), for processing waveforms for their functional control. Digital Signal Processor (104) can include one or many processors, such as but not limited to ASIC (application-specific integrated circuit), FPGA (field-programmable gate array), DSP (digital signal processor), AsAP (asynchronous array of simple processors), and other types of data processing architectures. Data & Control Bus (103) can also link System Controller (102), as well as Digital Signal Processor (104), to one or more display units with modules for user interfaces, e.g., Display (105) with a module User Interface (106) to provide information to a user or operator and to receive input/commands from the user or operator. Display (105) can include many suitable display units, such as but not limited to cathode ray tube (CRT), light emitting diode (LED), and liquid crystal display (LCD) monitor and/or screen as a visual display. Display (105) can also include various types of display, speaker, or printing interfaces. In other examples, Display (105) can include other output apparatuses, such as toner, liquid inkjet, solid ink, dye sublimation, inkless (such as thermal or UV) printing apparatuses and various types of audio signal transducer apparatuses. User Interface (106) can include many suitable interfaces including various types of keyboard, mouse, voice command, touch pad, and brain-machine interface apparatuses.

The exemplary system (100) can include Waveform Generator (107), which can be controlled by System Controller (102) for producing one or more digital waveforms. The one or more digital waveforms can be generated as analog electronic signals (e.g., analog waveforms) by at least one element in an array of waveform synthesizers and beam controllers, e.g., represented in this example as Waveform Synthesizer and Beam Controller (108). Waveform Generator (107) can be at least one of a function generator and an arbitrary waveform generator (AWG). For example, Waveform Generator (107) can be configured as an AWG to generate arbitrary digital waveforms for Waveform Synthesizer and Beam Controller (108) to synthesize as individual analog waveforms and/or a composite analog waveform. Waveform Generator (107) can also include at least one memory unit(s) that can store pre-stored waveforms and coefficient data and information used in the generation of a digital waveform.

The exemplary system (100) shown in FIG. 1A includes Waveform Synthesizer and Beam Controller (108) comprising I number of array elements. In one example, Waveform Synthesizer and Beam Controller (108) can be configured to include at least one waveform synthesizer element on each line of the I number of array waveform synthesizers. In another example, Waveform Synthesizer and Beam Controller (108) can include at least one beam controller element on each line of the I number of array beam controllers. In another example, Waveform Synthesizer and Beam Controller (108) can include at least one waveform synthesizer element and beam controller element on each line of the I number of array waveform synthesizers and beam controllers. Waveform Synthesizer and Beam Controller (108) can include a phase-lock loop system for generation of an electronic signal, e.g., a radio frequency (RF) waveform. An exemplary RF waveform can be synthesized by Waveform Synthesizer and Beam Controller (108) from individual waveforms generated in the array elements of Waveform Synthesizer and Beam Controller (108), e.g., one individual RF waveform can be generated in one array element substantially simultaneously to all other individual waveforms generated by the other array elements of Waveform Synthesizer and Beam Controller (108). Each individual RF waveform can be defined for a particular frequency band, also referred to as a frequency component or 'chip', and the waveform properties of each individual waveform can be determined by Waveform Generator (107), which can include at least one amplitude value and at least one phase value corresponding to the chip. Waveform Generator (107) can issue commands and send waveform data including information about each individual waveform's properties to Waveform Synthesizer and Beam Controller (108) for generation of individual RF waveforms that can be composited into a composite RF waveform.

The individual RF waveforms and/or the composite RF waveform generated by Waveform Synthesizer and Beam Controller (108) can be modified by Output Amplifiers (109), which includes an array of I number of amplifiers, e.g., by amplifying the gain and/or shifting the phase of a waveform. Output Amplifiers (109) can be used as transducer drivers. The individual RF waveforms and/or the composite RF waveform can be passed to Transmit/Receive (T/R) switch (110), e.g., an N-pole double-throw transmit/receive switch. T/R Switch (110) that can be interfaced with a transducer module. A generated RF waveform, e.g., the composite RF waveform and/or at least one individual RF waveform, that is to be transmitted into a target medium can be transduced into, for example, an acoustic wave by the transducer module that can include an array of transducer elements, e.g., Transducer Array (111) comprising I number of elements. For example, the transduced acoustic wave can be emitted in the form of an acoustic waveform pulse. Each array element of the Transducer Array (111) may generate one or more acoustic waveforms that correspond to the individual waveform chips determined by the Waveform Generator (107).

The exemplary transduced transmitted acoustic waveform can be transmitted toward a target area, e.g., biological tissue, and form a spatially combined acoustic waveform. The transmitted waveform can propagate into the target medium, which for example, can have one or more inhomogeneous mediums that partially transmit and partially reflect the transmitted acoustic waveform. Exemplary acoustic waveforms that are partially reflected, also referred to as returned acoustic waveforms, can be received by Transducer Array (111). For example, each array element of I array elements of Transducer Array (111) can be configured to receive a returned acoustic waveform corresponding to the frequency chip and convert it to an analog RF waveform. The individual received (analog) RF waveforms can be modified by Pre-Amplifier module (112), which includes an array of I number of amplifiers, e.g., by amplifying the gain and/or shifting the phase of a waveform. The individual received waveforms can be converted from analog format to digital format by analog to digital (A/D) Converter module (113), which includes an array of I number of A/D converters. A/D Converter module (113) can include A/D converters that have low least significant bit (LSB) jitter, spurious-free dynamic range (SFDR) and waveform dependency, such that the exemplary waveforms can be adequately decoded. The converted digital representations of the individual received waveforms can be processed by a processor, e.g., Digital Signal Processor (104), in manner that creates and forms a representative image of the target medium.

The exemplary system (100) can be operated in one of many operation modes. In one example, Master Clock (101) can provide the time base for synchronizing the system (100), e.g., as a time base for the Waveform Synthesizers (108). Master Clock (101) can be configured as a low phase noise clock such that the exemplary waveforms can be phase encoded. An operator can select the mode of operation at User Interface (106). Exemplary modes of operation provided for the user to select at the User Interface (106) include Conventional A-Mode (e.g., 1D Depth only image), Conventional B-Mode (e.g., 2D Plane image—transverse vs. depth), Conventional C-Mode (e.g., 2D Plane image at selected depth), and Conventional D-Modes (e.g., Doppler Modes). Exemplary Doppler modes include Color Doppler (e.g. superposition of color coded Doppler and B-mode images), Continuous Doppler (e.g., 1D Doppler profile vs. depth), Pulsed Wave Doppler (e.g., Doppler vs. time for selected volume), and Duplex/Triplex Doppler (e.g., superposition of Conventional B-Mode, Conventional C-Mode or Color Doppler, and Pulsed Wave Doppler). Some other exemplary modes of operations can include Conventional 3D and 4D ("real time" 3D) volume renderings of the previously described modes of operations. The exemplary system (100) can implement new modes of operation that can generate spread spectrum, wide instantaneous bandwidth, frequency- and/or phase-coded waveforms. For example, a user can select exemplary ATS-Modes (Artificial Tissue Staining Modes) that can comprise a B-Mode, a C-Mode, a D-Mode, or other mode combined with image color coding to aid tissue differentiation—analogous to tissue staining for microscopic histological studies; and exemplary CAD-Modes (Computer Aided Diagnostic Modes) that differentiate and identify tissue type. ATS-Modes can employ the use of features for image color coding in image processing based on one or more of a number of measured properties that are obtained from the returned echo waveform from the target area, e.g., the returned echo from an exemplary transmitted spread spectrum, wide instantaneous bandwidth, coded acoustic waveform. CAD-Modes can use classifiers (algorithms) to classify, for example, tissue types based on features of the measured properties of the returned echo from the target area, e.g., the returned echo from an exemplary spread spectrum, wide instantaneous bandwidth, coded acoustic waveforms. The features properties can include differing impedances, amplitude reflections (as a function of wavelength), group delay, etc. Some exemplary classifiers that can be employed using CAD-Modes can include deterministic classifiers, stochastic classifiers (e.g., Bayesian classifiers), and neural network classifiers.

Figure 1B:
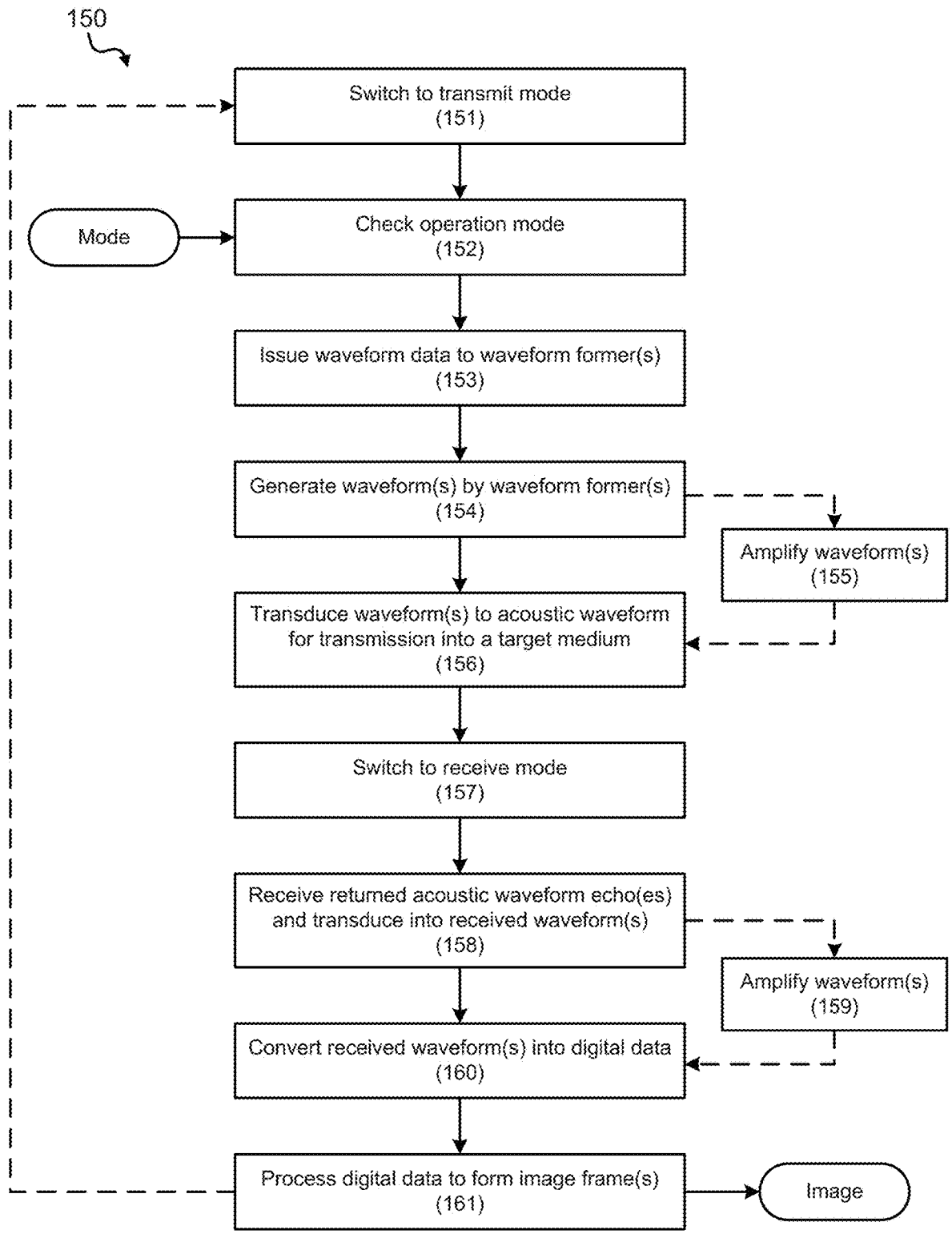
FIG. 1B shows a chart for operation of an exemplary ultrasound imaging system using spread spectrum coded waveforms.

FIG. 1B shows an exemplary operation process (150) for operating the system (100) for ultrasound imaging. For each time epoch, process (150) can begin by implementing process (151) to switch system (100) in transmit mode. For example, the System Controller (102) can command an N-pole double-throw T/R switch, e.g., T/R Switch (110), to transmit position. Process (150) includes a process (152) to check a user-defined mode of operation. For example, mode of operation can be selected by a user using User Interface (106), or the mode of operation can be selected by another entity or internally within system (100). Based on the selected operation mode, System Controller (102) can command Waveform Generator (107) to issue a digital message (data) to one or more elements in Waveform Synthesizers and Beam Controllers (108) that defines the frequency, amplitude and phase of each of the frequency chips that form a desired wideband composite RF waveform commanded, e.g., implemented in a process (153). Process (152) can occur anywhere and implemented in multiple instances during process (150). Process (150) includes a process (153) to issue waveform data (e.g., the exemplary digital message/data) to waveform synthesizers and beam formers, such as the Waveform Synthesizers and Beam Controllers (108). The issued waveform data can include the frequency, amplitude and phase information of the desired frequency chips that are synthesized as frequency- and/or phase-coded waveforms, in which each coded waveform corresponds to a distinct frequency band. Process (150) includes a process (154) to generate individual analog RF waveforms that correspond to defined frequency chips. For example, each element in the array of Waveform Synthesizers and Beam Controllers (108) can convert the digital message/data from the Waveform Generator (107) into individual analog waveforms that can make up a coherent analog wideband composite waveform. Process (150) includes a process (155) to amplify the individual analog waveforms that can make up a coherent analog wideband composite waveform. For example, each analog waveform and/or wideband composite waveform can be amplified by an array element in Output Amplifier (109). The amplified analog wideband composite waveform can then pass through the T/R Switch (110) and excite its respective array element of the Transducer Array (111) (e.g., in an ultrasound probe). Process (150) includes a process (156) to transduce the composite analog waveform to an acoustic waveform that can propagate throughout the scanned volume. For example, each element of the Transducer Array (111) can provide an acoustic waveform from each of the individual analog waveform corresponding to the frequency chip generated in Waveform Synthesizer and Beam Controller (108) that makes up the wideband composite acoustic waveform. Transducer Array (111) can form the acoustic beam that propagates into the target medium, e.g., biological tissue volume under study.

At the end of process (156), process (150) can implement process (157) to switch system (100) in receive mode. For example, the System Controller (102) can command the N-pole double-throw T/R Switch (110) to receive position. Process (150) includes a process (158) to receive a returned acoustic waveform, which can be in the form of one or more returned acoustic waveforms (also referred to as acoustic waveform echoes). Process (158) can also include transducing the returned acoustic waveform echo(es) into individual received analog waveforms, e.g., corresponding to the frequency chips of the generated individual waveforms. For example, the returned acoustic waveform propagates back to and is received by Transducer Array (111). Each element of Transducer Array (111) can convert the received acoustic waveform it receives into an analog signal (waveform). Process (150) includes a process (159) to amplify the individual received analog waveforms. For example, each received analog waveform can be amplified by its respective low noise pre-amplifier element in Pre-Amplifier module (112). Process (150) includes a process (160) to convert the individual received analog waveforms into digital waveform data. For example, each received (and amplified) analog waveform signal can be converted into a digital word by each respective A/D element in A/D Converter module (113). The digital format data can be sent to Digital Signal Processor (104) for signal processing. Process (150) includes a process (161) to process the digital waveform data into image frames representative of the target medium. Process (161) can also include compositing the digital waveform data into a composite digital signal representing the individual and composite received analog waveform. For example, Digital Signal Processor (104) can detect the amplitude and phase of each of the frequency chips that comprise the wideband composite acoustic waveform received by each of the transducer array elements. Digital Signal Processor (104) can form the received beam and separate the amplitude and Doppler components of each resolution element of the beam, and can form an image frame associated with mode previously selected by operator. The image frame formed by Digital Signal Processor (104) can be displayed on Display (105) to the user. For other subsequent time epochs, System Controller (102) can repeat this exemplary process, e.g., by commanding Waveform Generator (107) to issue to each element in Waveform Synthesizers (108) another digital message that defines the amplitude and phase of each of the frequency chips that comprise the wideband composite waveform and by commanding T/R Switch (110) back to transmit position, etc.

The system (100) can be implemented to produce spread-spectrum, wide instantaneous bandwidth (e.g., up to 100% or more of fractional bandwidth), coherent, pseudo-random noise (PRN), frequency- and/or phase-coded waveforms for ultrasound imaging. There are limitless embodiments of such waveforms. One example is featured in FIG. 2, which shows an exemplary plot of a generated composite waveform (200) that is comprised of a plurality of individual waveforms (e.g., frequency chips). In some implementations, the individual waveforms of the composite waveform (200) can be PRN waveforms including a sequence of pulses for each frequency chip that repeats itself after a sequence or code period (T), e.g., such that the sequence has a very low correlation with any other sequence in the set of frequency chips, or with the same sequence at a significantly different time frame, or with narrow band interference or thermal noise. For example, the system (100) can generate exactly the same sequences of the exemplary PRN waveforms at both the transmitter and the receiver ends, so a received signal sequence (based on the transmitted signal sequence) can exhibit a high correlation for signal processing to produce an acoustic image of the target.

Figure 2:
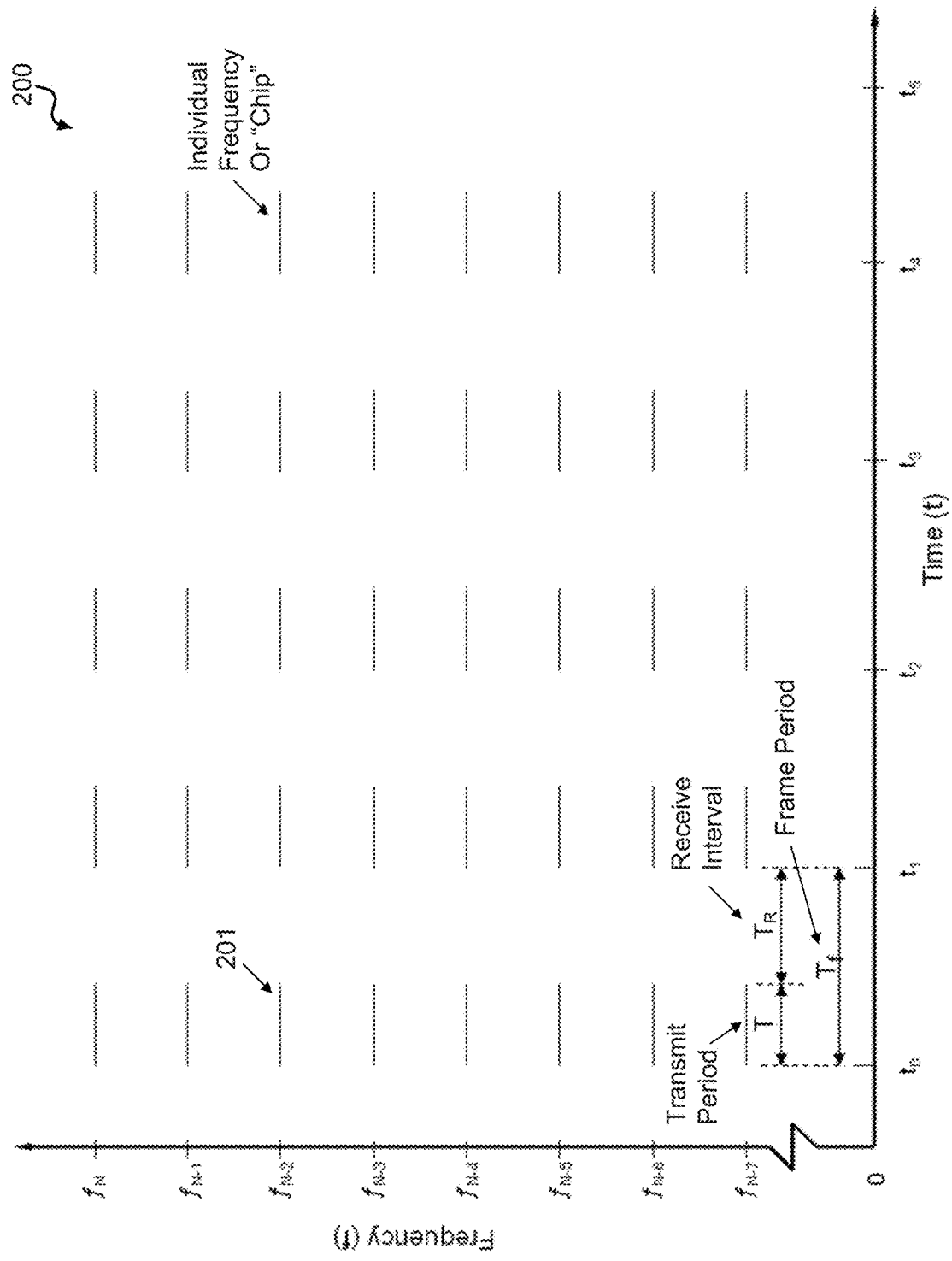
FIG. 2 shows a graph of an exemplary spread spectrum, wide instantaneous bandwidth, frequency- and/or phase-coded waveform featuring a plurality of waveforms.

As shown in FIG. 2, an exemplary individual waveform or chip (201) of the composite waveform (200) corresponds to the frequency chip $f_{N-2}$ that is transmitted during a transmit period T beginning at time frame $t_0$, e.g., as described in the process (156) in FIG. 1B. As shown in FIG. 2, following the transmit period T, a receive time interval $T_R$ is exhibited, in which returned acoustic waveform echoes are received as described in the process (158) in FIG. 1B.

The transmit period T and the receive time interval $T_R$ form a frame period $T_f$, which can be repeated in subsequent time frames ($t_1$, $t_2$, $t_3$, . . . ).

The exemplary composite waveform (200) can be represented by an equation for waveform, W, which can be represented in the time domain as a complex number, given by Equation (1):

$$W(t) = \sum_k \sum_n A_n e^{j(2\pi n f_0 t + \Phi_{nk} + C_n)} U(t - kT_f) \tag{1}$$

W is comprised of M individual orthogonal waveforms (e.g., orthogonal frequency chips), where $j=-\sqrt{-1}$. In Equation (1), T represents the chip duration or period of the coded sequence, and $f_0$ represents the fundamental chip frequency, such that $f_0=1/NT$, and in which $Nf_0$ is the maximum frequency and $(M-N+1)f_0$ is the minimum frequency. n represents a sequence of positive integers from $N-M+1$ to N. The waveform repetition frequency is $1/T_f$, with $T_f$ being the duration of a frame or epoch, and $U(x)=1$ for $0 \leq x \leq T_f$. $\Phi_{nk}$ represents the frequency chip phase term of the $n^{th}$ chip in the $k^{th}$ time epoch, and $A_n$ is the amplitude of the $n^{th}$ chip. The frequency chip phase term $\Phi_{nk}$ can be a pseudo-random phase term, in which a pseudo-randomly scrambled starting phase $\Phi_{nk}$ is a random number in the set $\{I_{nk} 2\pi/N\}$, where $I_{nk}$ is a sequence of random, positive integers selected without replacement from the series $I=0, 1, 2, 3, \ldots , N$, with N being a large number. $C_n$, which is an additive phase term, is a number between 0 and $2\pi$. For example, the frequency chip phase pseudo-random values $\Phi_{nk}$ can be pre-stored in an exemplary database within a memory unit of System Controller (102) and/or Waveform Generator (107).

The composite waveform, W, can be formed by synthesizing substantially orthogonal coded waveforms (e.g., frequency chips), in which each coded waveform corresponds to a distinct frequency band, and the coded waveforms includes at least one of frequency-coded waveforms or phase-coded waveforms, e.g., the coded waveforms synthesized in the Waveform Synthesizers (108). The coded waveforms can be synthesized as frequency-coded waveforms by selecting two or more frequencies that define the carrier frequencies of the frequency chips (e.g., including selecting the minimum and maximum frequency) and determining the $A_n$ amplitude values of the frequency chips. The synthesis of the frequency-coded can also include determining a time-bandwidth product ($Mf_0T$) parameter of each waveform of the coded waveforms. In some implementations, the amplitude for a particular frequency chip can be determined as a single value for that frequency chip during a particular time epoch and repeated in subsequent time epochs for the particular frequency chip. In other implementations, the amplitude for a particular frequency chip can be determined as a single value for that frequency chip during a particular time epoch and assigned a different single value in subsequent time epochs for the particular frequency chip. And in other implementations, the amplitude for a particular frequency chip can be determined to include multiple amplitude values for that frequency chip during a particular time epoch, in which the multiple values of the $A_n$ can be repeated or varied in subsequent time epochs for the particular frequency chip. The selection of the range of frequencies from the maximum frequency ($Nf_0$) to the minimum frequency ($(M-N+1)f_0$) plus the set of individual waveform amplitude terms ($A_n$) can utilize one of many known code sequences (e.g. including pushing sequences, Barker Codes, etc.) or, for example, utilize a numerical search on pseudo-random codes or any other codes for minimum ambiguity sidelobes.

The coded waveforms can additionally or alternatively be synthesized as phase-coded waveforms by determining individual waveform phase terms ($\Phi_{nk}$) of each waveform of the coded waveforms. For example, to provide variation of the composite waveform, W, the phase $\Phi_{nk}$ can include one or more phase values for a frequency chip within the transmit period T. In some implementations, the phase $\Phi_{nk}$ for a particular frequency chip can be determined as a single value for that frequency chip during a particular time epoch and repeated in subsequent time epochs for the particular frequency chip. In other implementations, the phase $\Phi_{nk}$ for a particular frequency chip can be determined as a single value for that frequency chip during a particular time epoch and assigned a different single value in subsequent time epochs for the particular frequency chip. And in other implementations, the phase $\Phi_{nk}$ for a particular frequency chip can be determined to include multiple values for that frequency chip during a particular time epoch, in which the multiple values of the $\Phi_{nk}$ can be repeated or varied in subsequent time epochs for the particular frequency chip. For example, the waveform (201) in the first time epoch ($t_0$) can include a first phase $\Phi_A$, for example, as its phase shift for the beginning portion of the transmit period T and a second phase $\Phi_B$, for example, as its phase shift for the latter portion of the transmit period T. The waveform (201) in the next time epoch ($t_1$) can repeat the exemplary phases $\Phi_A$ and $\Phi_B$ as its beginning and latter phase shifts or include another phase shift sequence (e.g., such as $\Phi_A$, $\Phi_B$, $\Phi_C$, or such as $\Phi_B$ and $\Phi_A$, or other configurations). The synthesis of the frequency-coded can also include determining a time-bandwidth product ($Mf_0T$) parameter of each waveform of the coded waveforms.

An exemplary transmitted waveform, W, can be comprised of the set of M individual waveforms that are orthogonal and completely span the frequency range $f_{N-M+1}$ to $f_N$, as seen in FIG. 2. The parameter N can be chosen to be a large number to give W a wide instantaneous bandwidth. In the special case when the lowest frequency $f_{N-M+1}=1/T$, then W can describe any wideband waveform that may be contained within this range of frequencies. For any waveform among the M individual waveforms, one or more phases (e.g., $\Phi_{nk}$) can be encoded in a single waveform during the interval T. Additionally, any waveform among the M individual waveforms can include multiple amplitudes encoded in a single waveform. This can be implemented by amplitude weighting and phase weighting.

The family of individual waveforms described by Equation (1) can form a coherent, pseudo-random noise, frequency- and/or phase-coded, spread spectrum composite waveform. Based on the selection of parameters, the individual waveforms can be made to be statistically orthogonal to any degree desired. For example, the sidelobe levels of the ambiguity function, described later in Equation (2), for a given waveform represents the degree of orthogonality of that waveform. By determining particular parameters of the waveforms, medical ultrasound image resolution can be significantly improved. For example, parameters that affect the resolution of medical ultrasound images include the time-bandwidth product ($Mf_0T$) parameter, which determines the inherent combined axial range (e.g., Doppler resolution) and the speckle reduction ability of the waveform, and the individual waveform phase terms ($\Phi_{nk}$), which determine the statistical degree of orthogonality, e.g., which in turn determines the degree that the waveform can function in inhomogeneous media of biological tissues. For example, the lower the sidelobes, the greater the orthogonality and greater the resolution (less noise). The selection of the set of individual waveform phase terms ($\Phi_{nk}$) can utilize one of many known code sequences (e.g. including Barker, Frank, Golay, etc.) or, for example, utilize a numerical search on pseudo-random codes or any other codes for minimum ambiguity sidelobes.

In some implementations, the composite waveform (200), e.g., described by Equation (1), can be a single wideband, coherent, frequency- and/or phase-coded waveform. For example, based on the selection of parameters, the single waveform can be made to be statistically orthogonal to any other signal waveform or noise signal present in the target medium.

The parameter $A_n$, which is the amplitude of the $n^{th}$ chip, and $C_n$, which is an additive phase term, in combination can provide pre-emphasis of the analog signal that excites each individual element of Transducer Array (111) to produce a transmitted acoustic waveform that has the desired amplitude and phase characteristics over the frequency range of W. Pre-emphasis of the transmitted waveform can compensate for both the non-constant amplitude and phase response of transducer elements as a function of frequency, and the non-uniform propagation characteristics of intervening tissue layers. For example, the pre-emphasis terms can provide an acoustic waveform that has equal amplitude chips with constant (e.g., flat) amplitude and a known phase versus frequency characteristic. Such constant amplitude versus frequency acoustic waveforms can be referred to as 'white' waveforms. Alternatively, if pre-emphasis is not provided, then the transmitted acoustic waveform can replicate the frequency response of the transducer, and such waveforms are referred to as 'colored' waveforms. De-emphasis of the received waveform can permit determination of the reflection characteristic of the target medium's volume, e.g., biological tissue volume.

By inspection, single frequency modes (e.g., Conventional A-, B- and C-Mode), due to their monochromatic nature, do not need pre-emphasis. Such single frequency waveforms may require amplitude control, for example, to ensure biologically safe sound intensity limits.

If the phase of each chip is random, the transmitted waveform, W, can have random noise-like characteristics. If the phases ($\Phi_{nk}+C_n$) of each chip are uniquely determined, repeatable and synchronized to the Master Clock (as shown in FIG. 1A), the transmitted waveform, W, can be classified as pseudo-random noise. Such pseudo-random noise waveforms are coherent permitting implementation of coherent receivers.

Image processing advantages of wide instantaneous bandwidth, pseudo-random noise waveforms can include reduction, with proper waveform selection, and potential elimination of speckle, e.g., speckles/speckle patterns, which are random intensity patterns produced by the mutual interference waveforms, which are commonly associated with conventional medical ultrasound images. This exemplary reduction in speckle can be an analogous comparison of a scene illuminated by wide band, Gaussian noise-like white light, which has no observable speckle to narrow band laser illumination with exhibits strong speckle of the same scene.

Signal processing advantages of coherent, pseudo-random noise, frequency- and phase-coded waveforms can include waveforms having very low time and Doppler sidelobes. For example, an ambiguity function, $A(\tau,\upsilon)$, can be a two-dimensional representation that shows the distortion of a received waveform processed by a matched filter in the receiver due to the effect of Doppler shift (υ) or propagation delay (τ). Specifically, the exemplary ambiguity function A(τ,υ) is defined by Equation (2) and is determined solely by the waveform properties and the receiver characteristics and not by the scenario. The ambiguity function of A(τ,υ) is defined by $$A(\tau, v) = \int_{-\infty}^{+\infty} X_a(t) X_b^*(t-\tau) e^{j2\pi vt} \quad (2)$$

where $X_k(t) = \frac{1}{\sqrt{T}} e^{j[2\pi f_k(t-t_k)+\Phi_k]}$, for $0 \le t \le T$, $X_k(t) = 0$ otherwise.

For waveforms of the type described by Equation (1), the following equation can be obtained:

$$A(\tau, v, t, f_n, \Phi_n, f_m, \Phi_m, T) = \quad (3)$$
$$\left(1 - \frac{|\tau - (\Delta t)|}{T}\right) \frac{\operatorname{Sin}[2\pi(\Delta f)(T - |\Delta t|)]}{[2\pi(\Delta f)(T - |\Delta t|)]} e^{j2\pi[\Delta f(T+\Delta t)-f_n\Delta t+vt+\Delta\Phi]}$$

where Δt=τ–t, Δf=υ–($f_n$–$f_m$), and ΔΦ=$\Phi_n$–$\Phi_m$, which can result in the complete ambiguity equation shown in Equation (4):

$$x(\tau, v) = \frac{1}{M} \sum_n \sum_m A(\tau, v, t, f_n, \Phi_n, f_m, \Phi_m, T) \quad (4)$$

where both n and m are a sequence of positive integers from N–M+1 to N.

Figure 3:
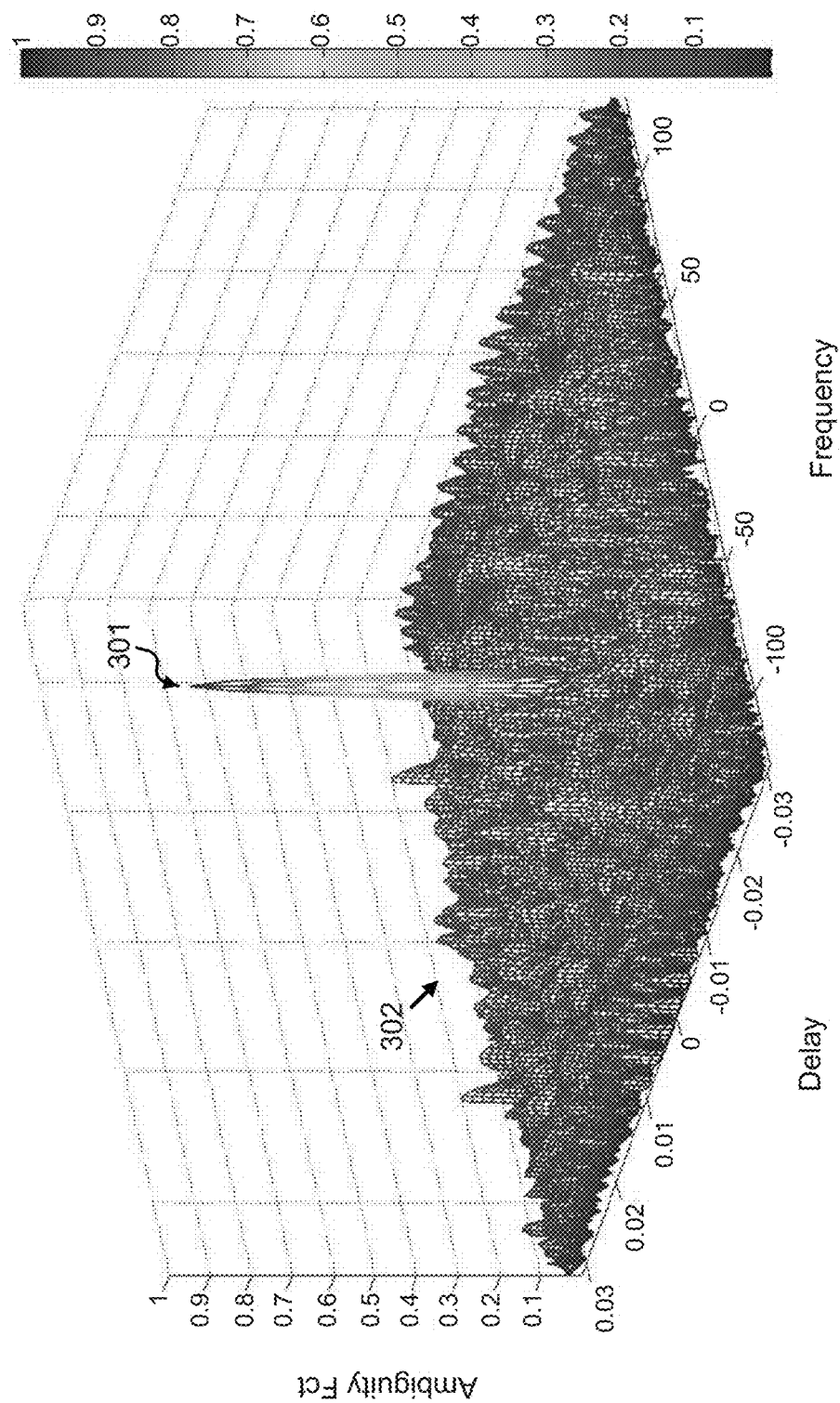
FIG. 3 shows ambiguity function characteristics of an exemplary spread spectrum coded waveform.

FIG. 3 shows exemplary ambiguity function characteristics of a pseudo-random noise, frequency-coded waveform (301), represented by an equation for waveform, W. The exemplary coded waveform (301) includes a code length of 128. As shown in FIG. 3, the sidelobes (302) of this ambiguity function are due to chip-to-chip phase interactions and have a plateau level below the peak that is a function of $N^2$.

By inspection, many waveforms (W) are possible depending on the specific random number codes ($I_{nk}$) selected. However, the sidelobe performance cannot be guaranteed for every waveform defined, and therefore only those codes which give sufficiently low sidelobes as determined by a numerical search of a set of possible codes should be used.

For example, in medical ultrasound applications, living tissue as a propagation medium is inhomogeneous. Propagation medium inhomogeneity can introduce differential time delays, and living tissue can introduce unwanted motion induced Doppler. Ultrasound transducer arrays also can have undesirable side lobes and grating lobes (e.g., due to physical size limitations) in the off axis portions of ultrasound beam that add unwanted time delay and Doppler returns to the returns of the main lobe. Waveforms that exhibit low ambiguity function sidelobes can significantly improve focusing and target contrast due through the reduction interference from differential time delays, motion induced Doppler, transducer side lobe effects.

Coherent pseudo-random noise, frequency- and/or phase-coded waveforms can enable higher order cross range focusing techniques to be employed that can improve the lateral resolution of size limited ultrasound transducer arrays, e.g., medical ultrasound transducer arrays.

For example, each biological tissue type and each diseased tissue types may exhibit their own unique ultrasound echo return as a function of frequency and spatial morphology. Using conventional Elastograph-Mode (E-Mode) modalities, it can be difficult to take advantage of such properties to classify tissues, e.g., due to measurement errors such as the inability to accurately characterize the ultrasound wave propagation through overlaying inhomogeneous media. Exemplary waveforms produced by the exemplary system (100), e.g., wide instantaneous bandwidth, coherent pseudo-random noise, frequency- and/or phase-coded waveforms, can enable tissue differentiation by simultaneously determining the propagation delay for each acoustic ray through intervening tissue layers and accurately determining the spatial echo features of the target volume under investigation. Classifiers, one example being Bayesian inference Classifiers among others, can be applied to the feature data obtained from the measured characteristics of the received echo to automatically classify tissue types observed in the target volume providing a Computer Aided Diagnostic-Mode (CAD-Mode).

Unlike conventional E-Modes, which inherently have significantly reduced image quality and rely on individual operator technique, the exemplary waveforms described by Equation (1) can inherently provide improved image quality while simultaneously colorizing the resultant image by tissue type in the ATS and/or CAD-Modes. With this advantage, user technique can be mitigated and the margins of a lesion are discernible thus permitting improved diagnoses.

Figure 4A:
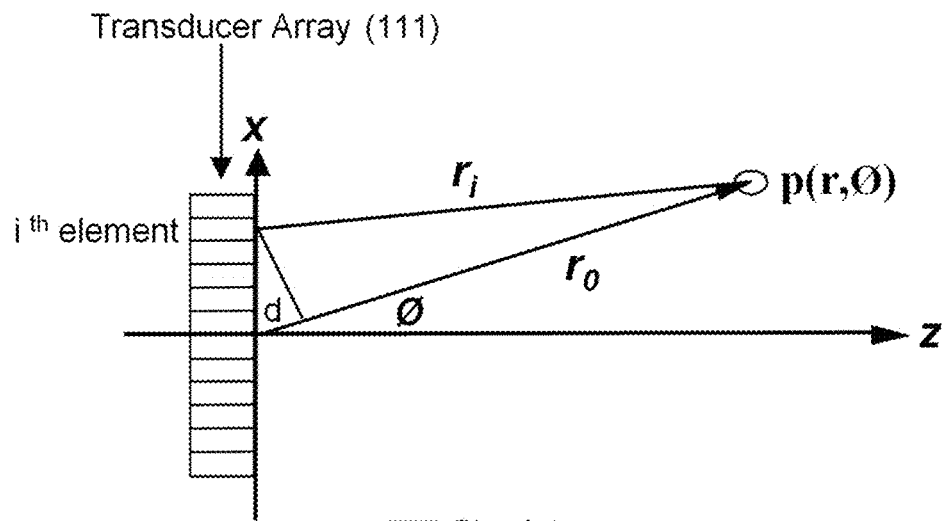
FIGS. 4A-4C show an exemplary diagram for beam steering, dynamic focusing, and forming.
Figure 4B:
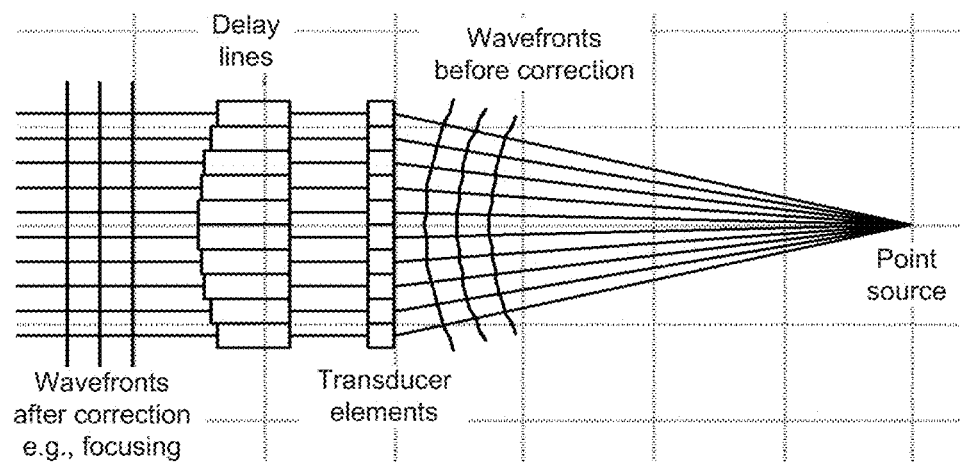
Figure 4C:
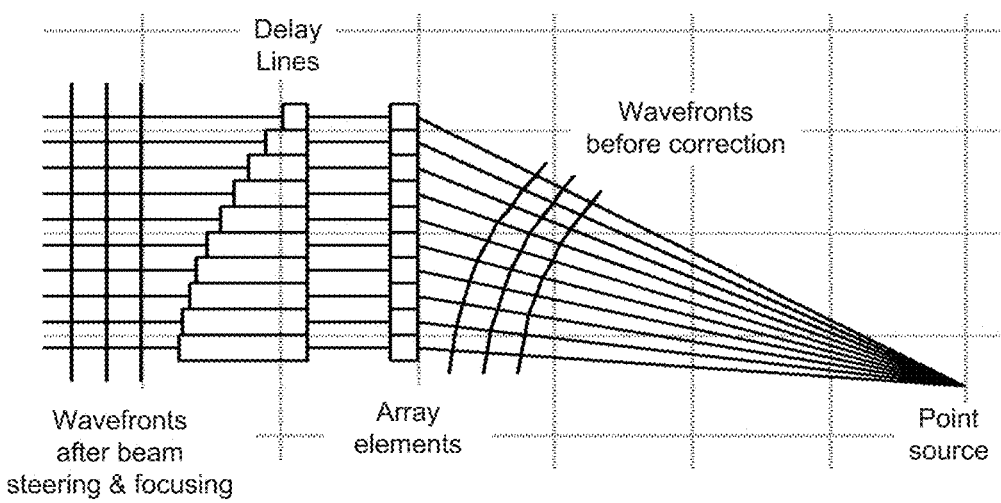

In addition, Waveform Synthesizers (108) positioned on transmit and Digital Signal Processor (104) positioned on receive (as shown in FIG. 1A), can also perform beam control (e.g., beam steering, dynamic beam focusing, and beam forming) functions. FIGS. 4A-4C show the basics of these digital electronic functions by introducing a differential time delay, or equivalently a phase shift, and amplitude weighting between each of the elements of the phased array. As can be seen in FIG. 4A, the differential phase shift can compensate for the differential change in distance (d) each acoustic ray ($r_1$, $r_2$, . . . $r_i$, . . . ) travels from $i^{th}$ element to the point of focus (p). An angle (θ) is formed as the point of focus (p) is not along the z-axis direction of direct aim/alignment of the Transducer Array (111) toward a target in the target medium. Additionally, a differential amplitude weight can be applied to each element to control the beam shape and suppress side and grating lobes. Also, for one or more chips in an exemplary waveform, Waveform Generator (107) can pre-encode a phase delay to delay the phase of the one or more chips transmitted at each transducer element in Transducer Array (111). An exemplary result of this feature can be seen in FIGS. 4B and 4C. The exemplary phase delay values for the one or more chips can be communicated to Digital Signal Processor (104) and/or System Controller (102) to incorporate the phase delay values in the signal processing of the received composite waveform.

For narrow instantaneous bandwidth ultrasound devices, this function can be accomplished by introducing phase shift and amplitude attenuation on the composite analog signal driving each element. However, for the exemplary spread-spectrum, wide instantaneous bandwidth, frequency- and phase-coded waveforms generated by system (100), each individual chip of the waveform ($W_i$) is individually amplitude weighted ($B_{ni}$) and phase weighted ($D_{ni}$) as a function of frequency (n) for each array element (i) individually for all I elements, as indicated by Equation (5).

$$W_i(t) = \sum_k \sum_n A_n B_{ni} e^{j(2\pi n f_0 t + \Phi_{nk} + C_n + D_{ni})} U(t - kT_f) \qquad (5)$$

On transmit, the amplitude and phase weighting required of each chip can be computed by the System Controller (102) and can be sent as an instruction to the Waveform Generator (107). Waveform Generator (107) can then send the digital words (real and imaginary components) to the Waveform Synthesizers and Beam Controller (108) that produces the analog drive signal that is amplified by Amplifier (109) and sent to each element of the array of Transducer Array (111).

On receive, the reverse process takes place. The A/D Converter module (113) can send the digital words that represent the amplitude and phase information of each chip for each array element to the Digital Signal Processor (104), which in turn can digitally form the receive beam for each chip.

Figure 5:
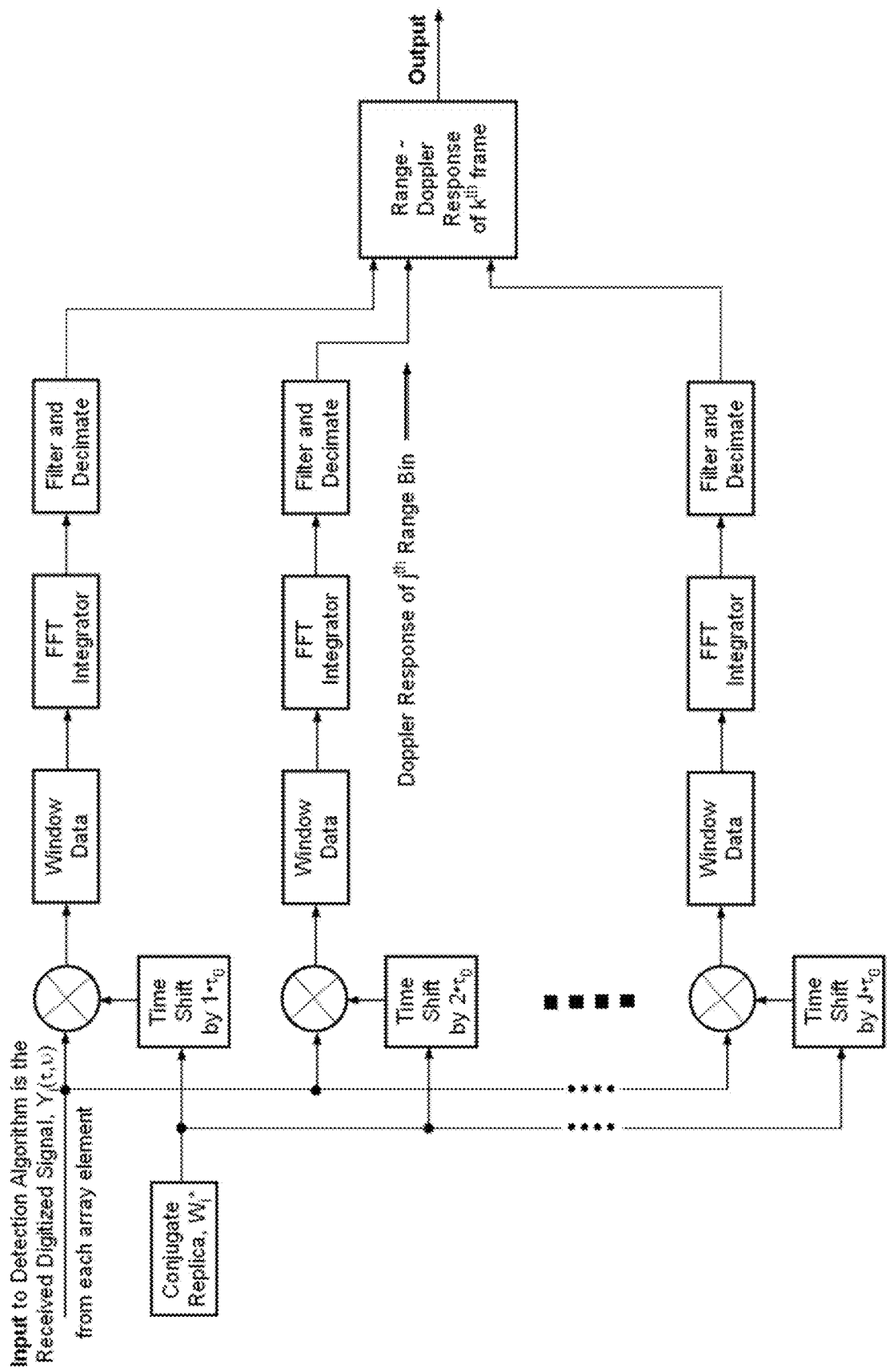
FIG. 5 shows an exemplary block diagram for correlation processing of a spread spectrum coded waveform.

A multitude of ways can be used to process the received waveforms, e.g., wide-bandwidth, spread-spectrum, frequency and/or phase-coded waveforms. FIG. 5 shows an exemplary correlation processing technique. For example, an input to the exemplary correlation processing technique can include a digitized received signal, $Y_i(\tau,\upsilon)$, which can be multiplied by the complex conjugate replica of the transmitted digital waveform, $W_i^*(\tau)$. The complex conjugate replica $W_i^*(\tau)$ can be time shifted by $1 \cdot \tau_0$ prior to multiplication. This multiplication operation can be repeated multiple times for multiple time shifts, e.g., J times, as seen in FIG. 5. The multiple multiplication operations for the multiple time shifts can be repeated in parallel, but for each operation the replica is shifted in time by an increment, $\tau_0$, from the previous one, as shown in the figure. For each time step, the resultant products can be filtered with a window function, such as a Hann, Hamming, Tukey, Kaiser Bessel, Dolph-Chebyshev, Blackman-Harris window, etc., a fast Fourier Transform (FFT) integrator, and passed through a digital filter. For example, a digital filter of a type that is dependent of the specific waveform, W, can be employed to filter and decimate the inputted signal. The exemplary process can result in the range-Doppler return for each individual $i^{th}$ element of the transducer array. The output data stream from the exemplary detection algorithm can then be processed using conventional techniques to form an image for display. The processed range and Doppler data and/or waveforms can be further processed by partitioning the I number of transducer elements into two or more subarrays. The processed range-Doppler return for the $i^{th}$ element can be weighted in amplitude and/or phase depending on which subarray that $i^{th}$ element belongs. These weighted returns can then be summed and differenced. These sum and differences can then be processed to improve the cross range image resolution of the system.

Several applications and uses of the disclosed technology can be implemented to exploit the described features of the aforementioned systems, methods, and devices. Some examples are described for clinical use of the disclosed technology.

In one exemplary application, the resultant image quality, the ATS and CAD modes of an exemplary spread spectrum ultrasound device can enable the primary care physician to incorporate this modality into a routine examination screening protocol to locate early stage malignancies (e.g., Stage 0 or 1), as well as later stage cancers. As the result of this application, the device can potentially, for example, enhance the survival rate of hard to diagnose asymptomatic patients suffering from such malignancies such as stomach, pancreatic, bladder cancers, etc.

In another exemplary application, the resultant image quality, ATS and CAD modes of an exemplary spread spectrum ultrasound device can permit board certified radiologists to diagnose neoplasms as benign or malignant prior to any surgical biopsy or resection intervention. As a result of this application, the ability of radiologists to locate and diagnose early stage malignancies (e.g., Stage 0 or 1) can potentially improve patient survival rate. Additionally, unnecessary biopsies can potentially be avoided, along with their attendant risk of hard to treat or even lethal complications such as, for example, methicillin resistant *Staphylococcus aureus* (MRSA staph) infections.

In another exemplary application, the resultant 3D image quality of an exemplary spread spectrum ultrasound device and its 4D imaging capability can be used in fine needle biopsy and other medical procedures. For example, the exemplary spread spectrum ultrasound device can be integrated into an exemplary fine needle biopsy instrument (e.g., with the device's transducer probe), which can permit the fine needle biopsy of very small, early stage (e.g., Stage 0 or 1) neoplasms to confirm noninvasive diagnoses. As a result of this application, the ability of surgeons to avoid open biopsies and the potential for hard to treat and lethal complications that may result is clearly beneficial to the patient.

In another exemplary application, the integration of this device's spread spectrum transducer probe with minimally invasive surgical high definition video instrumentation can permit the fusing of the optical and ultrasound images. Given the improved 3D image quality of this spread spectrum ultrasound device, its 4D imaging capability, the ATS and CAD modes, such fused video and ultrasound images can give surgeons the added ability to locate and surgically excise diseased tissue without excising excessive healthy tissue.

In another exemplary application, given the improved 3D image quality of this spread spectrum ultrasound device, its 4D imaging capability, and its ATS modes, an exemplary spread spectrum ultrasound device can reduce the amount of time for the brachytherapy treatment of malignant neoplasms by precisely guiding the insertion of catheters and sealed radioactive sources into the proper location. The application of this spread spectrum ultrasound device to brachytherapy can be especially useful for the treatment of small, hard to locate neoplasms and their margins.

In another exemplary application, given the improved 3D image quality of this spread spectrum ultrasound device, its 4D imaging capability, and its ATS modes, an exemplary spread spectrum ultrasound device can enable the effective insertion of high dose, localized pharmaceutical treatments of diseases by precisely guiding the insertion of catheters and pharmaceuticals into the proper location. The application of this spread spectrum ultrasound device to brachytherapy can be especially useful for the treatment of small, hard to locate neoplasms.

Implementations of the subject matter and the functional operations described in this specification, such as various modules, can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer program products, e.g., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, such as, for example, digital signal processors (DSP), and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this patent document.

What is claimed is:

1. A method for acoustic imaging, comprising:
   producing a composite waveform having a plurality of individual coded waveforms each corresponding to distinct frequency bands, wherein the producing of the composite waveform includes:
   generating a set of random numbers,
   selecting individual composite digital codes based on the generated set of random numbers, wherein each of the individual composite digital codes correspond to the individual coded waveforms in digital format, and
   forming the composite waveform from the selected individual coded waveforms;
   producing and transmitting a composite acoustic beam, based on the generated composite waveform, toward a material of interest, wherein the transmitting includes generating drive signals corresponding to the composite waveform to drive transducer elements of a transducer array to form the composite acoustic beam;
   receiving returned acoustic waveforms that are returned from at least part of the material of interest corresponding to at least some transmitted acoustic waveforms that form the composite acoustic beam; and
   processing the received returned acoustic waveforms to produce an image containing information of the material of interest.

2. The method of claim 1, wherein the generated set of random numbers includes random phases.

3. The method of claim 1, further comprising:
   storing the selected individual composite digital codes in memory of one or more computer devices.

4. The method of claim 1, wherein the selected individual coded waveforms include coherent waveforms.

5. The method of claim 1, wherein the selected individual coded waveforms include frequency-coded waveforms.

6. The method of claim 1, wherein the selected individual coded waveforms include phase-coded waveforms.

7. The method of claim 1, wherein at least one of the selected individual coded waveforms that form the composite waveform includes two or more amplitudes, two or more phases, or two or more amplitudes and two or more phases.

8. The method of claim 1, wherein at least some of the selected individual coded waveforms that form the composite waveform are individually amplitude weighted, thereby providing at least one of steering, focus, or forming of the composite acoustic beam.

9. The method of claim 1, wherein at least some of the selected individual coded waveforms that form the composite waveform are individually phase weighted, thereby providing at least one of steering, focus, or forming of the composite acoustic beam.

10. An acoustic imaging system, comprising:
a computing device comprising a processor and a memory and configured to produce a composite waveform having a plurality of individual coded waveforms each corresponding to distinct frequency bands, wherein the computing device is operable to produce the composite waveform by: generating a set of random numbers, selecting individual composite digital codes based on the generated set of random numbers, wherein each of the individual composite digital codes correspond to the individual coded waveforms in digital format, and forming the composite waveform from the selected individual coded waveforms;
a digital to analog (D/A) converter, in communication with the computing device, to convert the individual coded waveforms that form the composite waveform from the digital format to an analog format as an analog composite waveform;
an array of transducer elements, in communication with the D/A converter, to receive the analog composite waveform and transmit a composite acoustic beam toward a material of interest, wherein the array of transducer elements are operable to receive a returned acoustic waveform returned from at least part of the material of interest; and
an analog to digital (A/D) converter, in communication with the array of transducer elements, to convert the received returned acoustic waveform received by the array of transducer elements from an analog format to a digital format as a received composite waveform comprising information of the material of interest.

11. The system of claim 10, wherein the array of transducers are configured to acoustically couple to a receiving volume containing the material of interest, and wherein a transmission of the composite acoustic beam by the array of transducer elements includes generating drive signals corresponding to the composite waveform that drive the transducer elements of the array to create and propagate the composite acoustic beam in the receiving volume and toward the material of interest.

12. The system of claim 10, wherein the computing device includes a controller unit and a user interface unit in communication with the controller unit, wherein the controller unit is configured to process the received composite waveform to produce an image of at least part of the material of interest and display the image on the user interface.

13. The system of claim 10, wherein the generated set of random numbers generatable by the computing device includes random phases.

14. The system of claim 10, wherein the computing device is configured to store the selected individual composite digital codes in the memory.

15. The system of claim 10, wherein the selected individual coded waveforms include coherent waveforms.

16. The system of claim 10, wherein the selected individual coded waveforms include frequency-coded waveforms.

17. The system of claim 10, wherein the selected individual coded waveforms include phase-coded waveforms.

18. The system of claim 10, wherein at least one of the selected individual coded waveforms that form the composite waveform includes two or more amplitudes, two or more phases, or two or more amplitudes and two or more phases.

\* \* \* \* \*